United States Patent
Young et al.

(10) Patent No.: US 9,873,904 B2
(45) Date of Patent: *Jan. 23, 2018

(54) DETECTION OF ACID-PRODUCING BACTERIA

(71) Applicant: 3M INNOVATIVE PROPERTIES COMPANY, St. Paul, MN (US)

(72) Inventors: Robert F. Young, Savage, MN (US); Patrick A. Mach, Shorewood, MN (US); Michael E. Hughes, Burnsville, MN (US); Christine A. Binsfeld, Woodbury, MN (US); Jason W. Bjork, Cottage Grove, MN (US); Mara S. Celt, Red Wing, MN (US); Henry J. Lubrant, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 241 days.

This patent is subject to a terminal disclaimer.

(21) Appl. No.: 14/493,991

(22) Filed: Sep. 23, 2014

(65) Prior Publication Data

US 2015/0010941 A1   Jan. 8, 2015

Related U.S. Application Data

(62) Division of application No. 13/377,952, filed as application No. PCT/US2010/038569 on Jun. 15, 2010, now Pat. No. 8,846,334.

(60) Provisional application No. 61/187,107, filed on Jun. 15, 2009, provisional application No. 61/314,140, filed on Mar. 15, 2010.

(51) Int. Cl.
*C12Q 1/04* (2006.01)
*C12M 1/12* (2006.01)
*C12M 1/34* (2006.01)
*C12M 1/00* (2006.01)

(52) U.S. Cl.
CPC .............. *C12Q 1/04* (2013.01); *C12M 23/04* (2013.01); *C12M 23/20* (2013.01); *C12M 23/34* (2013.01); *C12M 25/06* (2013.01); *C12M 41/36* (2013.01)

(58) Field of Classification Search
CPC . C12Q 1/04; C12Q 1/34; C12Q 1/527; C12Q 1/6806; C12Q 1/6876; C12Q 1/689; A61K 31/327; A61K 31/351; A61K 31/4174; A61K 31/4184; A61K 31/4436; A61K 31/445; A61K 31/4525; A61K 31/453; A61K 31/522; A61K 31/702; A61K 31/7036; A61K 31/7056; A61K 31/7072; A61K 35/742; A61K 35/744; A61K 36/899; A61K 38/164; A61K 38/1732; A61K 38/1841; A61K 38/19; A61K 38/30; A61K 38/54; A61K 39/05; A61K 47/02; A61K 47/12; A61K 47/36; A61K 47/48023; A61K 47/48061; A61K 47/4813; C12M 23/20; C12M 23/34; C12M 25/06; C12M 41/36; C12M 1/04
USPC ........ 435/252.3, 254.21, 254.22, 254.23, 29, 435/288.7, 34
IPC ......................................................... C12Q 1/04
See application file for complete search history.

(56) References Cited

U.S. PATENT DOCUMENTS

| | | | |
|---|---|---|---|
| 4,528,269 A | 7/1985 | Sandine et al. | |
| 4,565,783 A | 1/1986 | Hansen et al. | |
| 5,089,413 A | 2/1992 | Nelson et al. | |
| 5,098,832 A | 3/1992 | Rambach | |
| 5,164,301 A | 11/1992 | Thompson et al. | |
| 5,448,652 A | 9/1995 | Vaidyanathan et al. | |
| 5,601,998 A | 2/1997 | Mach et al. | |
| 5,681,712 A | 10/1997 | Nelson | |
| 5,786,167 A | 7/1998 | Tuompo et al. | |
| 5,879,635 A | 3/1999 | Nason | |
| 6,022,682 A | 2/2000 | Mach et al. | |
| 6,153,400 A | 11/2000 | Matsumura et al. | |
| 6,243,486 B1 | 6/2001 | Weiss | |
| 6,756,225 B2 | 6/2004 | Bedingham et al. | |
| 7,150,977 B2 | 12/2006 | Restaino | |
| 7,223,364 B1 | 5/2007 | Johnston et al. | |
| 2004/0101954 A1 | 5/2004 | Graessle et al. | |
| 2004/0102903 A1 | 5/2004 | Graessle et al. | |

FOREIGN PATENT DOCUMENTS

| GB | 2 185 039 | 7/1987 |
|---|---|---|
| WO | WO 2005/024047 | 3/2005 |

OTHER PUBLICATIONS

Bujalance, C. et al.; "A selective differential medium for *Lactobacillus plantarum*"; Journal of Microbiological Methods: vol. 66; 2006; pp. 572-575.
Darukaradhya, J. et al.; "Selective enumeration of *Lactobacillus acidophilus, Bifidobacterium* spp., starter lactic acid bacteria and non-starter lactic acid bacteria from Cheddar cheese"; International Dairy Journal; vol. 16; 2006; pp. 439-445.
Davidson, C.M. et al.; "Medium for the Selective Enumeration of Lactic Acid Bacteria from Foods"; Applied Microbiology; vol. 26, No. 3; 1973: pp. 439-440.

(Continued)

Primary Examiner — Pablo S Whaley
Assistant Examiner — Kailash C Srivastava

(57) ABSTRACT

The disclosure provides culture devices and methods useful for detecting acid-producing bacteria in a sample. The devices include a nutrient medium and a pH indicator to detect and differentiate acid-producing microorganisms, such as lactic acid bacteria. Methods of use include detecting or enumerating acid-producing microorganisms. The methods further provide for the detection of gas-producing acid-producing bacteria.

15 Claims, 3 Drawing Sheets

(56) References Cited

OTHER PUBLICATIONS

Hall, P.A. et al.: "Chapter 19—Acid-Producing Microorganisms"; Compendium of Methods for the Microbiological Examination of Foods—Fourth Edition; 2001; Title, copyright, table of contents and chapter 19 (pp. 201-207); 20 pgs.

James, G.A. et al.; "Digital Image Analysis of Growth and Starvation Responses of a Surface-Colonizing *Acinetobacter* sp."; Journal of Bacteriology; vol. 177, No. 4; pp. 907-915.

McDonald, L.C. et al.; "A Differential Medium for the Enhancement of Homofermentative and Heterofermentative Lactic Acid Bacteria"; Applied and Environmental Microbiology; vol. 53, No. 6; 1987; pp. 1382-1384.

McGregor, J.U. et al.; "A Research Note—Recovery of Lactic Acid Bacteria on Petrifilm™ SM Under Various Incubation Atmospheres"; Journal of Food Protection; vol. 57, No. 3; 1995; pp. 316-318.

Brochure entitled "Membrane Biofuouling and BIOCIDE use for Control"; Avista Technologies (UK) Ltd; 2002; 4 pgs.

Brochure entitled "3M Petrifilm™ Plates—Environmental Monitoring Procedures" #70-2008-2412-9 (33.5)ii; 2003; 4 pgs.

Brochure entitled "3M Petrifilm™ Aerobic Count Plate—Interpretation Guide"; #70-2008-6505-4 (46.2)ii; 2006; 6 pgs.

Brochure entitled "3M Petrifilm™ Aerobic Count Plates for Lactic Acid Bacteria"; #70-2009-3271-6 (90.8) DPI; 2000; 2 pgs.

Brochure entitled "3M Petrifilm™ Aerobic Lactic Acid bacteria Procedure—Instructions and Interpretation Guide"; rev1 Apr. 2009; 3 pgs.

Brochure entitled "3M Petrifilm™ Coliform Count Plate—Interpretation Guide"; #70-2008-4573-6 (1291.2) DPI; 1999; 6 pgs.

Brochure entitled "Interpretation Guide—3M Petrifilm™ Aerobic Count Plate Use for Growing Lactic Acid Bacteria": #70-2008-6506-4: 1998; 4 pgs.

Brochure entitled "3M Microbiology Technical Bulletin—3M™ Petrifilm™ Aerobic Count Plate Method for Lactic Acid Bacteria"; TB.029.00; 2008; 2 pgs.

Brochure entitled "3M MicroMessenger—3M Lactic Acid Test Meets Food Processors' Needs"; #70-2009-4026-3 (418) DPI; 2001; 4 pgs.

Brochure entitled "3M Redigel™ MRS test for lactic bacteria"; FOD# 1407; #34-7045-1234-1;1999; 4 pgs.

Brochure entitled "Multiple Testing Procedures": FOD #0401: #70-2008-6506-4: 2000; 3 pgs.

Brochure entitled "Fluka—02538 Raka Roy Agar, Base (Lactic Acid Bacteria Selective Agar, Base)"; 2 pgs.

DETECTION OF ACID-PRODUCING
BACTERIA

CROSS REFERENCE TO RELATED
APPLICATIONS

This application is a division of U.S. Ser. No. 13/377,952, filed Dec. 13, 2011 (now U.S. Pat. No. 8,846,334), which is a national stage filing under 35 U.S.C. 371 of PCT/US2010/038569, filed Jun. 15, 2010, which claims priority to U.S. Provisional Patent Application Nos. 61/187,107, filed Jun. 15, 2009; and 61/314,140, filed on Mar. 15, 2010; which are incorporated herein by reference in their entirety.

BACKGROUND

Acid-producing bacteria comprise a relatively diverse group of Gram positive microorganisms that share common metabolic and physiological characteristics. This group of bacteria produces acid as the major end product of the fermentation of carbohydrates. The group is divided into two metabolic subgroups—homolactic fermenters, which convert carbohydrates essentially into acid; and heterolactic fermenters which, in addition to producing acid, also convert carbohydrates into other metabolites including ethanol and carbon dioxide, for example.

Although some acid-producing bacteria, such as lactic acid-producing bacteria (LAB) have a beneficial role in the production of fermented foods, they also are known as a principal agent of food and beverage spoilage, particularly in vacuum-packaged meats, meat products, and beer. The metabolic activity of acid-producing bacteria in certain food products can lead to significant deterioration of the organoleptic properties (e.g., smell, taste) of the food or beverage.

Traditional microbiological techniques are typically used to identify and/or enumerate acid-producing bacteria, such as LAB. Agar and broth culture media (e.g., MRS and APT media) are used to promote growth and/or identify acid-producing bacteria. The cultures are incubated in microaerophilic environments to improve the growth of the acid-producing bacteria, such as LAB. Typical methods include the growth and isolation of presumptive acid-producing bacteria colonies on a selective agar plate, followed by subculture in a broth medium containing a fermentation tube to detect the production of gas by heterolactic fermenting species. These methods may take up to four days to detect or identify the acid-producing bacteria. In some cases, the methods may take from 7-10 days to identify the acid-producing bacteria.

There exists a need for simple articles and methods for the detection of acid-producing bacteria, such as LAB, in a sample.

SUMMARY

In view of the current general methods to detect and/or identify acid-producing bacteria, which typically require specialized culture media, lengthy incubation periods, specialized incubation conditions, and/or subculture procedures, the present disclosure includes simple articles and methods to detect and/or identify acid-producing bacteria. In some embodiments, the inventive methods provide for the differentiation of acid-producing bacteria. Additionally, or alternatively, some embodiments provide for the enumeration of acid-producing bacteria. In some embodiments, the inventive methods provide for the automated detection and/or enumeration of acid-producing bacteria.

Thus, in one aspect, the present disclosure provides a method of detecting a acid bacterium. A method of detecting acid-producing bacteria can comprise providing a thin film culture device, a culture medium to support the growth of acid bacteria, a pH indicator with a transition range that extends below pH 7.0, a carbohydrate that can be fermented by acid-producing bacteria, and a sample. The thin film culture device can comprise a cold water-soluble gelling agent. The method further can comprise combining, in the culture device, a predetermined volume of the sample, the culture medium, the pH indicator, and the fermentable carbohydrate. The method further can comprise incubating the culture device for a period of time at a pH below 7 and detecting the presence or absence of an acid-producing microorganism.

In another aspect, a method of detecting acid-producing bacteria is provided, comprising providing a thin film culture device comprising a cold water-soluble gelling agent, a culture medium to support the growth of acid-producing bacteria, a pH indicator with a transition range that extends below pH 7.0, a carbohydrate that can be fermented by acid-producing bacteria, and a sample suspected of containing acid-producing bacteria. The method further can comprise combining a predetermined volume of sample and the culture medium to form a first mixture; combining, in the culture device, the first mixture, the pH indicator, and the fermentable carbohydrate; incubating the culture device for a period of time; and detecting the presence or absence of a microorganism.

In any of the above embodiments, the culture device can comprise the culture medium and/or the pH indicator. In some embodiments of the method, the culture device further can comprise a selective agent. In some embodiments of the method, incubating the culture device can comprise incubating the device aerobically and/or anaerobically.

In any of the above embodiments, detecting the presence of a microorganism can comprise differentiating a microorganism. In some embodiments, differentiating a microorganism can comprise detecting a pH indicator reaction or detecting a gas bubble associated with the microorganism. In any of the above embodiments, the method further can comprise combining the sample with a diluent capable of neutralizing a chemical sanitizer. In any of the above embodiments, the pH of the culture medium can be adjusted to a pH below 6.5, wherein detecting the presence or absence of a microorganism comprises detecting the presence or absence of an acid-producing microorganism.

In any of the above embodiments, the method can further comprise providing an antifungal agent. In any of the above embodiments, the pH indicator can be selected from the group consisting of, for example, chlorophenol red, bromcresol purple, bromphenol blue and bromcresol green. In any of the above embodiments, the method can further comprise the step of enumerating microorganisms.

In any of the above embodiments, the method further can comprise providing an imaging system and obtaining an image of the culture device, wherein detecting the presence or absence of a microorganism comprises displaying, printing, or analyzing the image of the culture device. In some embodiments, the method further can comprise providing an image analysis system, wherein analyzing the image comprises analyzing the image with the image analysis system.

In another aspect, the present disclosure provides a thin film culture device. The culture device can comprise a body member comprising a self-supporting, water-proof substrate having upper and lower surfaces. The culture device can further comprise a dry coating on the upper surface of the substrate. The dry coating can comprise a culture medium to support the growth of acid-producing bacteria; a cold water-soluble gelling agent; a pH indicator with a transition range that extends below pH 7.0; and, optionally, an antifungal agent. In some embodiments, the culture device further can comprise a cover sheet. In some embodiments, the cover sheet further can comprise a coating that includes a cold water-soluble gelling agent and/or an indicator. In any of the above embodiments, the device can further comprise a carbohydrate that can be fermented by acid-producing bacteria. In any of the above embodiments, the pH indicator can be selected from the group consisting of, for example, chlorophenol red, bromcresol purple, bromphenol blue, and bromcresol green. In any of the above embodiments, the culture medium can comprise polyoxyethylene (20) sorbitan monooleate or sodium acetate. In any of the above embodiments of the culture device, the pH of the culture medium can be adjusted to a pH below 6.5.

In yet another aspect, the present disclosure provides a kit. The kit can comprise a thin film culture device comprising a cold water-soluble gelling agent, a culture medium to support the growth of acid-producing bacteria, a carbohydrate that can be fermented by acid-producing bacteria, and a pH indicator. In some embodiments, the culture medium of the kit can comprise an antifungal agent. In some embodiments, the culture medium of the kit can comprise the pH indicator or the carbohydrate that can be fermented by acid-producing bacteria. In some embodiments, the culture device of the kit can comprise the culture medium, the carbohydrate that can be fermented by acid-producing bacteria, the pH indicator, or a combination of any two or more of the foregoing. In any one of the above embodiments, the kit further can contain a sample preparation accessory selected from the group consisting of a sample diluent, a buffer, a sample acquisition device, and a pipette. In any of the above kit embodiments, the pH of the culture medium can be adjusted to a pH below 6.5.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a sample suspected of containing "a" microorganism can be interpreted to mean that the sample can include "one or more" microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further explained with reference to the drawing figures listed below, where like structure is referenced by like numerals throughout the several views.

DETAILED DESCRIPTION

Figure 1:
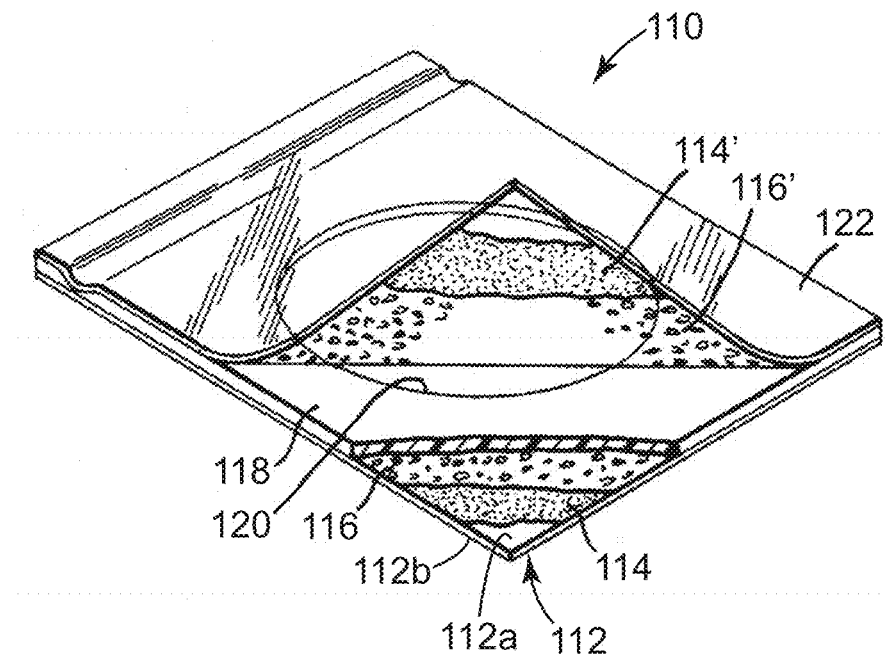
FIG. 1 is a top perspective view, partially in section, of an embodiment of a thin film culture device.

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways. Also, it is to be understood that the phraseology and terminology used herein is for the purpose of description and should not be regarded as limiting. The use of "including," "comprising," "containing," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure is generally directed to methods and articles for detecting and differentiating acid-producing bacteria in a sample. Described as facultative anaerobes, acid-producing bacteria are often cultivated in environments (e.g., chambers) from which oxygen is removed (e.g., catalytically removed). The inventive methods provide for growth, detection, and differentiation of acid-producing bacteria in oxygen-containing and/or low pH environments. The methods described herein can be used in anaerobic or aerobic environments, potentially eliminating the need for specialized incubation equipment. Additionally, the inventive methods provide for the differentiation of acid-producing bacteria by detecting the production of carbon dioxide gas from individual colonies, thus eliminating the additional incubation time needed for isolation of pure cultures and the use of fermentation tubes to detect gas production. Furthermore, the disclosure relates to the enumeration of acid-producing bacteria in a sample. In some embodiments, detection of acid-producing bacteria comprises automated detection using an imaging system.

Suitable samples can be obtained or derived from a variety of sources. The term "source" is generally used to refer to the food or nonfood desired to be tested for microorganisms. The source can be a solid, a liquid, a semi-solid, a gelatinous material, gas (e.g., air), and combinations thereof. In some embodiments, the source can be provided by a capture element that was used, for example, to collect the source from a surface of interest or from air. In some embodiments, the liquid composition can include the capture element, which can be further broken apart (e.g., during an agitation or dissolution process) to enhance retrieval of the source and any microorganism of interest. The surface of interest can include at least a portion of a variety of surfaces, including, but not limited to, walls (including doors), floors, ceilings, drains, refrigeration systems, ducts (e.g., air ducts), vents, toilet seats, handles, doorknobs, handrails, countertops, tabletops, eating surfaces (e.g., trays, dishes, etc.), working surfaces, equipment surfaces, clothing, etc., and combinations thereof. All or a portion of the source can be used in the method. When a portion of the source is used, this can sometimes be referred to as a "sample" of the source. However, the term "sample" is generally used herein to refer to the portion of volume or mass of material that is obtained from the source and is introduced into a test device for the detection of microorganisms.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, beer, animal feed, other suitable comestible materials, and combinations thereof.

"Sample acquisition device" is used herein in the broadest sense and refers to an implement used to collect a liquid, semisolid, or solid sample material. Nonlimiting examples of sample acquisition devices include swabs, wipes, sponges, scoops, spatulas, tongue depressors, filters, pipettes, pipette tips, and siphon hoses.

The term "fomite" is generally used to refer to an inanimate object or substrate capable of carrying infectious organisms and/or transferring them. Fomites can include, but are not limited to, cloths, mop heads, towels, sponges, wipes, eating utensils, coins, paper money, cell phones, clothing (including shoes), doorknobs, etc., portions thereof, and combinations thereof.

The term "acid-producing bacteria" is generally used to refer to any prokaryotic microorganisms that are characterized by their production of acid as a major metabolic end-product of carbohydrate fermentation. Examples of acid-producing bacteria include, but are not limited to, *Acetobacter* and LAB. The most common acid-producing bacteria include lactic acid-producing bacteria.

The term "lactic acid-producing bacteria" or "LAB" is generally used to refer to any prokaryotic microorganisms that are characterized by their production of lactic acid as a major metabolic end-product of carbohydrate fermentation. Examples of lactic acid bacteria include, but are not limited to, members of the following genera—*Streptococcus, Enterococcus, Lactobacillus, Pediococcus, Lactococcus, Aerococcus, Carnobacterium, Oenococcus, Sporolactobacillus, Tetragenococcus, Vagococcus,* and *Weissella.* Lactic acid bacteria include certain pathogenic bacteria such as, for example, vancomycin-resistant *Enterococcus,* certain species of the genus *Leuconostoc,* and *Streptococcus pyogenes.*

Environmental factors that may affect the growth of acid-producing bacteria can include the presence or absence of nutrients, pH, moisture content, oxidation-reduction potential, antimicrobial compounds, temperature, atmospheric gas composition and biological structures or barriers.

Culture Devices:

The present disclosure in certain embodiments includes culture devices for the detection of acid-producing bacteria, such as lactic acid-producing bacteria. Culture devices of the present invention include, for example, thin film culture plate devices. Thin film culture plate devices are typically more compact than traditional agar petri dishes and typically contain dry, rehydratable culture medium to support the growth of certain microorganisms. Non-limiting examples of thin film culture plate devices include the coated-substrate devices disclosed in U.S. Pat. Nos. 4,565,783; 5,089,413, and 5,681,712; each of which is incorporated herein by reference in its entirety.

Figure 2:
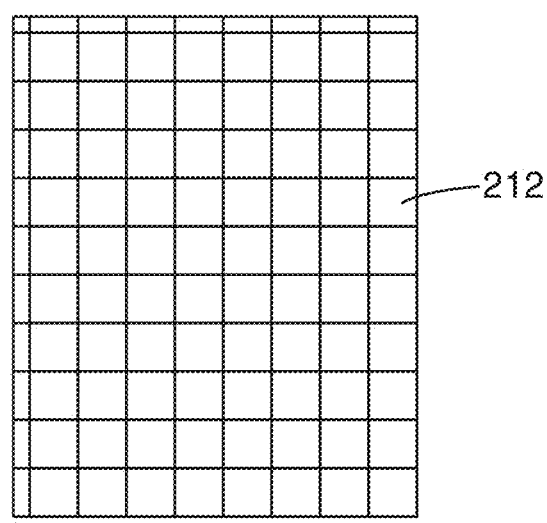
FIG. 2 is a top view of one embodiment of a self-supporting substrate comprising a grid pattern.

FIG. 1 illustrates an embodiment of a thin film culture device in accordance with the present invention. The culture device 110 includes a body member comprising a self-supporting water-proof substrate 112 having upper and lower surfaces (112a and 112b, respectively). Substrate 112 can be a relatively stiff film (e.g., polyester, polypropylene or polystyrene), which will not absorb or otherwise be affected by water. The substrate 112 may be either transparent or opaque, depending on whether one wishes to view bacterial colonies through the substrate. To facilitate the counting of bacterial colonies, the substrate 212 can have a grid pattern (e.g., squares) printed thereon, as shown in FIG. 2.

Referring to FIG. 1, substrate 112 can be coated on its upper surface 112a with a layer of an adhesive 114 which serves to hold the dry gelling agent, pH indicator, carbohydrate, optional antifungal agent, other indicators, and/or other nutrients in a uniform monolayer 116 for easy hydration. Adhesive 114 should be coated onto substrate 112 in a thickness which is preferably less than the diameter of the particles of the powdered gelling agent and/or nutrients. The object is to apply enough adhesive to adhere the particles to the substrate but not so much that the particles become completely embedded in the adhesive. A uniform monolayer of cold-water-soluble powder 116 is desired with sufficient surface area exposed for hydration. Also shown in FIG. 1 are optional adhesive 114' and cold-water-soluble powder 116' layers on cover sheet 122. When hydrated with an aqueous solution (e.g., the sample and/or an aqueous suspending medium, such as water or a buffer), the gelling agent forms a hydrogel.

In some embodiments, adhesive 114, 114' can comprise a water-based adhesive composition. Preferably, the layer of water-based adhesive 114, 114' is sufficiently transparent when wetted by an aqueous test sample to enable the viewing of the colonies of microorganisms. The water-based adhesive composition can incorporate one or more hydrophilic agents, including nutrients, selective agents, indicators (e.g., pH indicators), or combinations thereof.

The specific nutrients and/or selective agents used in the water-based adhesive composition will be apparent to those skilled in the art in view of the present specification and may be optimized for the particular acid-producing bacteria to be grown and/or to be selectively detected or inhibited. For example, certain selective agents (e.g., antibiotics such as vancomycin) may be added to the composition to select for corresponding antibiotic-resistant microorganisms. Additionally, the concentration of the selective agent can be adjusted to select for a certain level of resistance, which is well known to a person of ordinary skill in the art.

In a preferred embodiment useful with fermented food and beverages, the selective agent includes an antifungal agent. Useful antifungal agents include Cycloheximide, Nystatin, and Natamycin (also known as pimaricin). Other useful antifungal agents may be Amphotericin B and Filipin.

Nutrient media for culturing acid-producing bacteria are known in the art. Nonlimiting examples of such media include MRS medium, APT medium, tryptone glucose, beef extract medium, tryptone glucose yeast extract medium, tomato juice agar, and Kang-Fung medium. These and other nutrient media are suitable for use in devices and methods of the present disclosure, provided the components of the nutrient medium do not interfere with the detection (either visual or automated) of a change in the pH indicator due to the production of acid by the microorganisms. Suitable nutrient media include media that, after preparation, vary according to their respective pH. For example, tryptone glucose beef extract medium can have a pH of about 7.0±0.2, APT medium can have a pH of about 6.7±0.2, MRS medium can have a pH of about 6.5±0.2, tomato juice agar can have a pH of about 6.1±0.2.

In a preferred embodiment, the pH of the nutrient media can be adjusted to a lower pH. For example, in the brewing industry, it is desirable to have a nutrient media with a pH of less than about 6.8 and greater than about 3.5+/−0.2. In a particularly preferred embodiment, an MRS nutrient medium for the detection of acid-producing bacteria, particularly LAB, in beer can have a pH of 5.8+/−0.2. In another preferred embodiment the nutrient medium can have a pH of 6.5+/−0.2.

Suitable indicators for use in devices and methods of the present disclosure include pH indicators with a transition range that extends below pH 7.0. Nonlimiting examples of suitable pH indicators include halochromic compounds with a transition pH range that extends below the pH of the inoculated culture medium. A suitable pH indicator will have a transition pH range that extends far enough below the pH of the inoculated medium to detect (visually and/or by using an imaging system) a change in the pH indicator in or adjacent to a growing colony of acid-producing bacteria. Preferably, the pH indicator will have a transition pH range with a low endpoint that is not less than 0.25 pH units below the pH of the inoculated culture medium. More preferably, the pH indicator will have a transition pH range with a low endpoint that is not less than 0.5 pH units below the pH of the inoculated culture medium. Even more preferably, the pH indicator will have a transition pH range that extends not less than 1.0 pH unit below the pH of the inoculated culture medium. Most preferably, the pH indicator will have a transition pH range with a low endpoint that is about 3.5. Nonlimiting examples of suitable pH indicators include bromcresol purple, bromphenol blue, chlorophenol red, and bromcresol green.

An exemplary useful class of indicators include dyes that are metabolized by, or otherwise react with, growing microorganisms, and in so doing cause the microbial colonies to be colored or fluoresce for ease of detection and/or quantitation by a technician or by an automated reader. Nonlimiting examples of such dyes include triphenyltetrazolium chloride, p-tolyltetrazolium red, tetrazolium violet, veratryl tetrazolium blue, and 5-bromo-4-chloro-3-indolyl phosphate disodium salt. However, it will be appreciated that other suitable dyes can be used depending on the particular organism(s) to be identified. It will be appreciated by a person of ordinary skill in the art that any indicator, dye, selective agent, enzyme substrate, or nutrient used in accordance with the present invention should not substantially interfere with the observation and/or imaging of the pH indicator described herein.

A pH adjusting agent such as hydrochloric acid or sodium hydroxide may be used in some embodiments to adjust the pH of either the media or the prepared sample. In an alternate embodiment, a buffering reagent, such as sodium carbonate, can be employed to provide a medium exhibiting a neutral pH and "Cab-O-Sil M-5" can be employed as a processing aid, as described in U.S. Pat. No. 4,565,783, which is incorporated herein by reference in its entirety. Of course, the particular coating mixture (e.g., nutrients, indicators, and/or gelling agents) used for powder 116 may be adjusted depending upon the type of microorganisms to be grown.

It is contemplated that articles of the present disclosure can include differential indicators. As used herein, "differential indicator" refers to a reagent added to the medium that will indicate the presence of certain microorganisms and not other microorganisms. Nonlimiting examples of differential indicators include dyes (e.g., stains, pH indicators, redox indicators), enzyme substrates (e.g., chromogenic or fluorogenic substrates for phosphatases, glycosidases, peptidases, nucleases, lipases, and the like), and specific nutrients (e.g., fermentable carbohydrates, amino acids) which, when metabolized by certain microorganisms, produce a detectable reaction (e.g., a pH indicator changing color within or adjacent a colony).

In some embodiments, one or more differential indicators can be added to the thin film culture device in the water-based composition that is coated onto the substrate. In some embodiments, one or more differential indicators can be added to the liquid sample that is added to the culture device. In some embodiments, one or more differential indicators can be added to the culture device, after hydration of the culture device. An example of a method involving the use of a differential indicator added to the culture device after hydration is the method wherein an article for the detection of thermonuclease is added to the culture device after incubation such as described in U.S. Pat. No. 6,022,682 which is incorporated herein by reference in its entirety.

It is also contemplated within the scope of the invention that powder 116 may optionally include reagents necessary for carrying out certain biochemical tests for microorganism identification. Such reagents (e.g. an enzyme substrate), which undergo a color change in the presence of a particular type of microorganism, may be included in the powder 116 or adhesive 114.

In another embodiment of the invention, powder 116 may comprise a coating that includes a mixture of a gelling agent and a nutrient, a selective agent, and/or an indicator (e.g., a redox indicator, a pH indicator, an enzyme substrate) which has been dissolved or suspended in a solution, coated and dried onto substrate 112. In this embodiment, the coating is substantially water-free (i.e., the coating has a water content no greater than about the water content of the dehydrated coating once it has been permitted to equilibrate with the ambient environment).

In another preferred embodiment of the invention, powder 116 may comprise a coating that includes a mixture of a dry gelling agent, pH indicator, carbohydrate, optional antifungal agent, other indicators, and/or other nutrients which has been dissolved or suspended in a solution, coated and dried onto substrate 112. In this embodiment, the coating is substantially water-free.

As depicted in FIG. 1, the body member can include a spacer 118 applied to the upper surface of substrate 112, the spacer 118 comprising a circular aperture 120 cut through the center to expose the powder 116 on substrate 112. The walls of aperture 120 provide a well of predetermined size and shape to confine the medium following hydration. The aperture 120 generally delineates the growth area of the culture device 110. Spacer 118 should be thick enough to form a well of the desired volume, e.g., 1, 2 or 3 milliliters. Closed cell polyethylene foam or polystyrene foam are preferred materials for spacer 118, but any material which is hydrophobic (non-wetting), inert to microorganisms, and capable of withstanding sterilization may be used. In some embodiments (not shown), the spacer 118 can comprise a plurality of apertures 20 (e.g., 2, 3, 4, 5, 6, 7, 8, 9, 10, 12, 15, or 20 apertures), each of which can be inoculated with a distinct liquid sample.

Spacer 118 can include relatively thick designs, such as those described in U.S. Pat. No. 5,681,712, which is incorporated herein by reference in its entirety. One purpose of the thicker apertured spacer 118 is to locate and protect membranes (e.g. microporous filter membranes) placed in the aperture 120 of the spacer 118 (not shown). Another purpose of the thicker spacer 118 is to reduce or prevent contact by cover sheet 122 with the growing colonies of microorganisms (i.e., provide a "head space" between the growth surface and the cover sheet 122, which can also provide increased aeration for growing colonies of microorganisms).

The thickness of spacer 118 should be sufficient to enclose the liquid volume added to the culture device when the device is inoculated. Depending upon the thickness of the membrane, when used, the spacer can be at least about 0.5 mm thick, about 1 mm thick, about 1.5 mm thick and about 2 mm thick.

Figure 3:
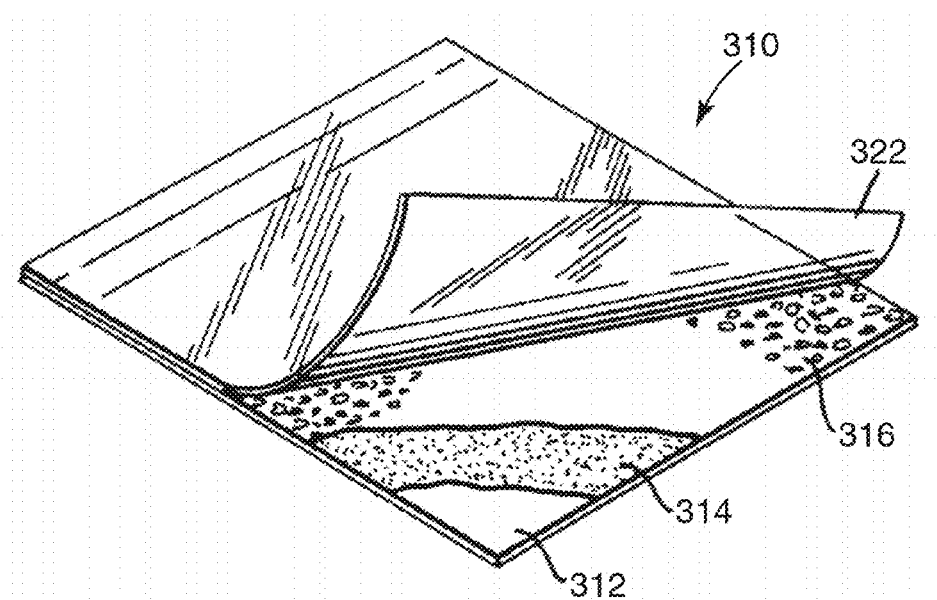
FIG. 3 is a top perspective view, partially in section, of an embodiment of a thin film culture device.

FIG. 3 shows another embodiment of a thin film culture device 310. This embodiment includes substrate 312, adhesive 314, cold-water-soluble powder 316, and cover sheet 322, as described in FIG. 1. In some embodiments, the pH indicator may be included in the cold-water soluble powder 316.

In contrast to the culture device 110 of FIG. 1, the device 310 of FIG. 3 does not include a spacer to confine the sample during inoculation. A template, e.g., a weighted ring (not shown), may be applied temporarily to the outside of cover sheet 322, after closing, to confine the sample to a specific region while the cold-water-soluble powder 316 forms a gel. The portion of the culture device 310 inoculated with a sample generally delineates a growth area of the device 310. In some embodiments, the device 310 can be inoculated with a plurality (e.g., 2, 3, 4, 5, 6, 7, 8, 9, 10, 12, 15, or 20) of distinct liquid samples, using appropriate spacing and templates to confine the separate samples to distinct portions of the powder 316 of the culture device 310. When hydrated with an aqueous solution (e.g., the sample and/or an aqueous suspending medium, such as water or a buffer), the cold-water soluble powder comprising a gelling agent forms a hydrogel.

Figure 4:
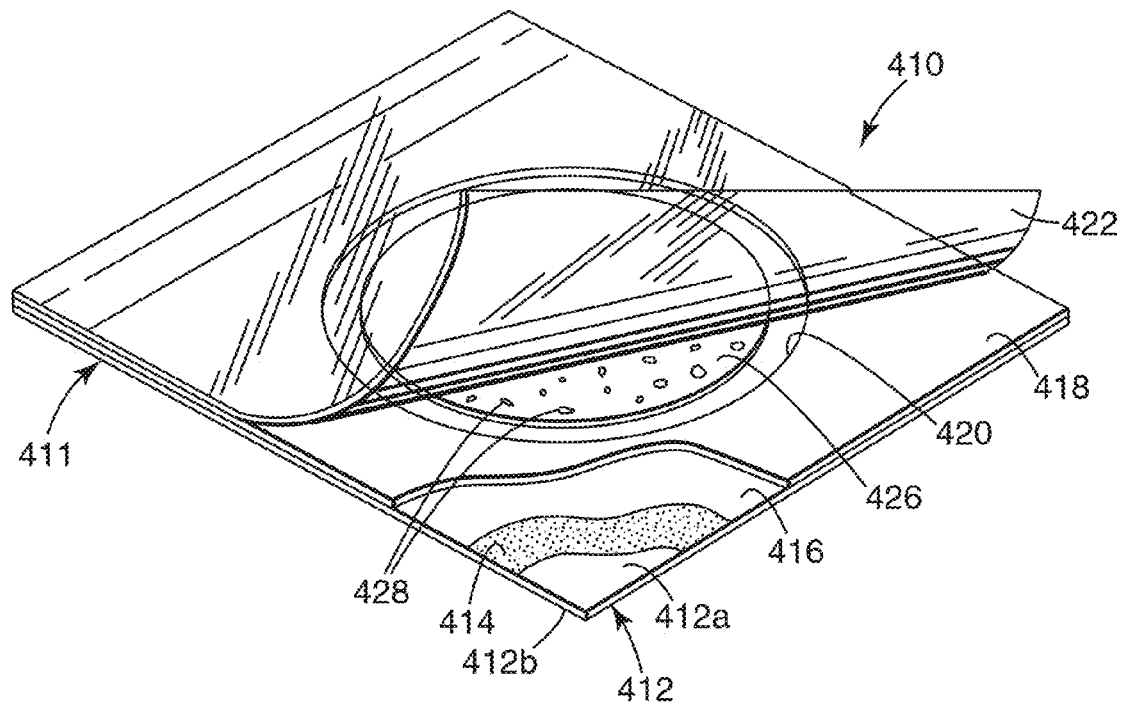
FIG. 4 is a top perspective view, partially in section, of an embodiment of a thin film culture device comprising a spacer and a capture element.

In one embodiment, a thin film culture plate device can be made by producing a liquid coating mixture, coating the liquid coating mixture onto a substrate, drying the coated substrate and, optionally, attaching a cover sheet according to processes described in U.S. Pat. No. 4,565,783, for example. An exemplary device of this embodiment is shown in FIG. 4. The thin film culture device 410 includes a body member 411 having a self-supporting, waterproof substrate 412 having upper and lower surfaces 412*a* and 412*b*, respectively. Substrate 412 is preferably a relatively stiff material made of a waterproof material that does not absorb water such as polyester, polypropylene, or polystyrene. Other suitable waterproof materials include substrates such as paper containing a waterproof polyethylene coating. The upper surface 412*a* is coated with a liquid composition, which is then dried to provide a dry coating 416 on substrate 412. The dry coating 416 comprises a cold-water soluble gelling agent as described herein and may also include a nutrient such as carbohydrate, a selective agent such as an antibiotic or antimycotic, an indicator, a pH indicator, or a combination of any two or more of the foregoing. The liquid composition used to produce the dry coating 416 may be readily dried by heating liquid composition in an oven at about 220° F. until essentially all of the water in the composition has evaporated. If the composition is heated after the water has evaporated, however, certain components of the composition (e.g., nutrients, indicators) may begin to degrade. In use, the dry coating 416 is hydrated with a liquid (e.g., a liquid sample and/or a liquid nutrient medium) to form a reconstituted liquid composition. When referring to the pH of a culture medium or nutrient media in dry form, the pH is measured with reference to the applicable dry coating after rehydrated with de-ionized water.

A layer of adhesive 414 may be coated on substrate 412. The adhesive may serve to hold the dry coating 416 to the substrate 412. The adhesive should be sufficiently transparent when hydrated to allow viewing of bacterial colonies growing on the surface of the coated substrate 412. The adhesive should also be coated on the substrate 412 in a thickness which allows the substrate to be uniformly coated with dry coating 416 without completely embedding the coating in the adhesive.

A spacer 418 having a generally circular aperture 420 is adhered to the dry coating 416 and/or the substrate 412. The spacer 418 covers the periphery of substrate 412 and the aperture 420 defines the area that is to be inoculated with a sample. Spacer 418 circumscribes the growth area of the device 410 and serves to prevent a liquid sample from leaking from the substrate 412. In an alternative embodiment, device 410 may not include a sample-containing spacer 418. In this device (not shown), the sample can be contained on the substrate during inoculation using the weighted circular template described above and is contained during incubation by the components (e.g., the gelling agent) of the medium alone.

A cover sheet 422 is attached to an edge of an upper surface of the foam spacer 418. Cover sheet 422 is preferably made of a transparent film or sheet material in order to facilitate counting of bacterial colonies present on the substrate. In addition, cover sheet 422 is preferably impermeable to bacteria and water vapor in order to avoid the risk of contamination and deterioration of the components. A preferred material for use as a cover sheet 422 is biaxially-oriented polypropylene. Optionally, the coversheet 422 may be coated with a layer of adhesive, which may be coated with a dried composition (e.g., powders) comprising a gelling agent, nutrients, selective agents, an indicator (e.g., a pH indicator), or a combination of any two or more of the foregoing (not shown).

In use, a predetermined amount of inoculum, typically about one milliliter of a liquid inoculum is added to the device illustrated in FIG. 4 by pulling back cover sheet and distributing the inoculum onto the dry coating 416. The inoculum may optionally comprise a nutrient, a selective agent, an indicator or a combination of any two or more of the foregoing. Cover sheet 422 is then replaced over the coating 417 and the inoculum is evenly spread inside the circular opening of the foam spacer 418. A convenient tool to do this is a weighted circular template. As the inoculum contacts and is spread on coating 417, the coating hydrates to form a gel. Nutrients present in the gel can support the growth of microorganisms. The inoculated device is then incubated for a predetermined time after which the number of bacterial colonies growing on the substrate may be observed through the transparent cover sheet 422 and counted.

A capture element, such as a membrane filter, can optionally be used with device 410. FIG. 4 shows a membrane filter 426 positioned in the aperture 420 of the spacer 418. Also shown are microorganism colonies 428 growing on the membrane filter 426. Suitable microporous membranes do not substantially interfere with the production of acid by the acid-producing bacteria or with the detection of acid using the pH indicator. In certain preferred embodiments, the microporous membranes are substantially transparent when contacted with the reconstituted liquid composition. The membrane filter 426 can be positioned in the device 410 before liquid is added to the device 410 to reconstitute the dry coating 416. The membrane filter 426 can be positioned in the device 410 after liquid is added to the device 410 to reconstitute the dry coating 416. In some embodiments, the membrane filter 426 may comprise enough liquid to reconstitute the dry coating 416 when the filter 426 is positioned in the device 410.

A preferred coating mixture, when hydrated with a predetermined volume of sample, can comprise the ingredients of the culture medium at the concentrations shown in Table 1. In some embodiments, the coating mixture for the culture device can comprise some of the ingredients shown in Table 1 and a liquid (e.g., a diluent) containing the sample can comprise some or all of the remaining ingredients shown in Table 1. Thus, the addition of the ingredients in the culture device and the ingredients in the diluent can result in the culture medium shown in Table 1. In one embodiment, the coating mixture comprises all of the ingredients.

TABLE 1

Composition of an exemplary culture medium.

| Ingredient | Amount (milligrams/mL) |
| --- | --- |
| Tryptone | 3.3 |
| Proteose Peptone No. 3 | 10 |
| Bacto Peptamin | 10 |
| Yeast Extract | 7.3 |
| Dextrose | 20.6 |
| Sodium Pyruvate | 6.6 |
| Beef Extract | 15 |
| $K_2HPO_4$ | 3.3 |
| $KH_2PO_4$ | 0.4 |
| Chlorophenol red | 0.21 |
| Polysorbate 80 | 6.0 |
| Ammonium citrate | 2.0 |
| Sodium acetate | 5.0 |
| Magnesium sulfate | 0.1 |
| Manganese sulfate | 0.05 |
| Lethicin | 0.7 |
| Sodium Chloride | 5 |
| Guar gum | 25-50 |

The culture medium of the present invention may include nutrients, salts and ions generally suitable to promote the growth of target (e.g., lactic acid-producing) microorganisms when the culture medium is inoculated with a sample suspected of containing the target microorganisms. The culture medium may include components from media that are used to culture the acid-producing bacteria. Exemplary media for the growth of acid-producing bacteria include, without limitation, MRS medium, Acidified MRS medium, Acidified MRS medium with fructose, Modified MRS medium, HHD medium, APT medium, APT medium with sucrose, APT medium with glucose, Universal Beer Agar (UBA), Nachweis medium fur Bierschadlichen Bakterien (NBB), and Raka-Ray.

TABLE 2

Composition of an exemplary MRS culture medium

| Ingredient | Grams per liter |
| --- | --- |
| Pancreatic Digest of Gelatin | 10 gm |
| Beer Extract | 8 gm |
| Yeast Extract | 4 gm |
| Dextrose | 20 gm |
| Dipotassium phosphate | 2 gm |
| Polysorbate 80 | 1 gm |
| Sodium Acetate | 5 gm |
| Ammonium Citrate | 2 gm |
| Magnesium Citrate | 0.2 gm |
| Manganese Sulfate | 0.05 gm |

Culture media containing components such as, for example, nutrients, salts, ions, selective agents, indicators, and the like can be tested with known acid-producing bacteria to determine that the components promote the growth of the target microorganism, inhibits the growth of non-target microorganisms, and/or does not interfere with the production of acid by the acid-producing bacteria or with the detection of lactic acid using the pH indicator. The culture medium also may include one or more gelling agents. The culture medium of the present disclosure can include at least one selective agent that selects for growth of acid-producing bacteria.

Optionally, the culture medium can comprise a buffer. Suitable buffers include phosphate buffers. In some embodiments, the carbonate buffer is a sodium carbonate buffer. In some embodiments, the phosphate buffer is a potassium phosphate buffer. In some embodiments, the culture medium can comprise more than one buffering agent (e.g., potassium phosphate and sodium acetate). The phosphate buffer can be about 22 mM. Other suitable buffers include Butterfield's Buffer, and peptone water, For some cultures, the combination of a buffer used with a particular culture medium can be advantageous. For example, MRS medium with a 1% peptone water buffer solution has been found useful for some acid-producing bacteria.

The concentration of each component in the culture medium is selected to provide a concentration suitable for growth and/or detection of the target microorganisms after the culture device has been inoculated. Suitable concentrations of nutrients and selective agents for growing acid-producing bacteria in culture media are known in the art.

Suitable concentrations of pH indicators may be influenced by their intrinsic properties (e.g., solubility and their potential inhibitory properties toward certain target microorganisms). For example, chlorophenol red can be used in the culture medium at a concentration of about 0.25 mM to about 0.75 mM. Preferably, chlorophenol red can be used in the culture medium at a concentration of about 0.5 mM. Also for example, bromcresol purple or bromcresol green can be used in the culture medium at a concentration of about 0.5 mM.

The selection of target microorganisms may include inhibiting the growth of non-target microorganisms, promoting the growth of non-target microorganisms, or both. Promoting the growth of target microorganisms may be provided by the at least one first selective agent either directly (e.g., a nutrient that can be used by target microorganisms and not by other microorganisms), indirectly (e.g., by reducing competition for nutrients by inhibiting non-target microorganisms), or both directly and indirectly.

Any element, radical, ion, or compound that selects for the growth of target microorganisms may be suitable for use as a selective agent. For example, suitable selective agents for acid-producing bacteria include but are not limited to Tween 80, sodium nitrite, polymyxin B, and any combination of two or more of the foregoing.

A dry culture medium according to the present invention may be applied to one or more surfaces of a thin film culture device in the following manner. The components of the culture medium may be dissolved in a solvent (e.g., water). The resulting solution may then be coated onto one or more surfaces of the device. The coating is then allowed to dry, leaving dried culture medium on the surfaces of the device that had been coated with the culture medium solution. The coating may be dried in any suitable manner including, but not limited to, air drying and heating.

The quantity of each component of the dry culture medium is at least partially determined by at least two factors: (1) the concentration of that component in the culture medium solution, and (2) the amount of the solution coated onto a given surface area of the culture device (the coating weight). Suitable coating weights may range from about 0.45 mg/cm$^2$ to about 2.5 mg/cm$^2$. In some embodiments, the culture medium nutrients may be coated separately from the indicators. In such embodiments, the coating weight for the culture medium nutrients may range from about 1.6 mg/cm$^2$ to about 2.5 mg/cm$^2$. In one embodiment, the coating weight of the nutrient coating is about 2.1 mg/cm$^2$. The coating weight for the indicator coating may range from about 0.45 mg/cm$^2$ to about 0.84 mg/cm$^2$. In one embodiment, the coating weight of the indicator coating is about 0.62 mg/cm$^2$.

Although the embodiments illustrated in FIGS. 1-4 have a cover sheet attached to the device, it is also contemplated within the scope of the invention that the powder-containing embodiments may be uncovered and simply placed in a sterile environment during storage and incubation.

Samples

Suitable test samples can be derived from any source. Samples of interest may include liquids (e.g., beverages, process streams, water, beer), solids (e.g., food ingredients, plants, meat, air, surfaces (e.g., floors, walls, instruments, food-processing equipment), and the like. Samples can also include cultured cells (e.g., bacterial cultures, enrichment broths).

Various sampling techniques for the detection of microbes on surfaces are known. Such sampling techniques are suitable for the methods of the present invention as well. For example, it is common to obtain a sample from wiping the surface of food processing equipment or from wiping the nares of a patient. A particularly preferred sampling technique includes contacting (e.g., swabbing, wiping) the surface with a sterile swab, sponge, or sampling device.

A wide variety of swabs or other sample collection devices are commercially available, for example, from 3M Company, St. Paul Minn., under the trade designation 3M™ Quick Swab, from Puritan Medical Products Co. LLC, Guilford, Me., under the trade designation PURE-WRAPS or from Copan Diagnostics, Inc. Corona, Calif., under the trade designation ESWAB, or from microRheologics, S.r.l., Brescia, IT, under the trade designation FLOCKEDSWAB. A sample collection means such as that disclosed, for example, in U.S. Pat. No. 5,879,635 (Nason) can also be used if desired. Swabs can be of a variety of materials including cotton, rayon, calcium alginate, Dacron, polyester, nylon, polyurethane, and the like.

The sample collection device (e.g., swab) can then be cultured directly, analyzed directly, or extracted (e.g., by washing, elution by vortexing) with an appropriate solution. Such extraction (i.e., elution) solutions typically include water and can optionally include a buffer and at least one surfactant. An example of an elution buffer includes, for example, phosphate buffered saline (PBS), which can be used in combination, for example, with TWEEN 20 or PLURONIC L64. The test sample (e.g., liquid) may be subjected to treatment prior to further analysis. This includes concentration, precipitation, filtration, centrifugation, dialysis, dilution, inactivation of natural components, addition of reagents, chemical treatment, etc.

Capture Element

Culture plate devices of the present disclosure can be used with a capture element to detect acid-producing microorganisms present in a sample. As used herein, "capture element" refers to an article that is used to capture and retain microorganisms that are present in a sample. In some embodiments, the capture elements can be contacted transiently with the thin-film culture plate devices disclosed herein. For example, the sample may be captured on one side of a surface filter and that side of the filter can be contacted with growth area of the thin-film culture plate device, and thereby transfer sample material to the growth area, after the culture plate device has been hydrated. The surface filter can then be removed from the device prior to incubating the device. The capture element (e.g. a membrane filter) can be dimensioned to allow it to be placed into a thin film culture plate device of the present invention and, in certain preferred embodiments, the capture element remains in the thin film culture plate device during the incubation period for a sufficient period to allow for at least one cell division of the target microorganism. Placing the capture element into the culture plate device can bring the capture element in contact with a gelling agent and/or a culture medium, if present, in the culture plate device, allowing microorganisms to grow and/or proliferate. In some embodiments, the culture plate device is hydrated (e.g., inoculated with a sterile liquid or an unknown liquid sample) before the capture element is placed into the culture plate device. In some embodiments, the culture plate device is hydrated after the capture element is placed into the culture plate device.

Capture elements can be selected for their suitability with certain types of samples. For example, microporous membrane filters can be used as capture elements to retain microorganisms present in a liquid sample. The liquid sample can be passed through the filter and the microorganisms can be retained thereon. Microorganisms can be retained by, for example, physical entrapment or specific (e.g., antigen-antibody or receptor-ligand interaction) or nonspecific (hydrophobic adsorption) chemical interaction. Microporous membranes of the present disclosure, when present in the thin-film culture plate device, should permit the observation of a hemolytic reaction. Preferred microporous membrane filters become substantially transparent when wet.

Referring to the embodiment shown in FIG. 4, the test sample may comprise a liquid inoculum and/or a capture element 426 such as a microporous filter (e.g., a filter membrane) or a wipe device. Capture element 426 can be constructed from various membranes and/or films and can be used to capture microorganisms. In some embodiments, capture element 426 can provide a surface on which the colonies of microorganisms can be grown, detected and/or enumerated by the method and devices of the invention. Particularly suitable are known microporous filters which have been commonly used to separate small microorganism populations, such as bacteria from large fluid samples. Such filters are known to be placed on the surface of agar media and incubated to allow counting and evaluation of the filtered microbes. Suitable filters include the HAWG series, e.g., HAWG 047S6 type HA filter, available from Millipore Corp (Marlborough, Mass.). The microorganism filters described herein are generally relatively thin and may be provided in any desired 2-dimensional shape, e.g., as rectangles, as discs (including partial discs) and the like.

Microorganisms are separated by such filters with varying efficiency depending upon the sizes of the pores in the membranes. Bacteria are typically captured by filters having a mean pore diameter of less than about 1 µm, less than about 0.8 µm, preferably, less than about 0.45 µm, more preferably, equal to or less than about 0.2 µm. Filtration is carried out by conventional methods using gravity or vacuum-assisted methods with funnels and discs of suitable sizes. Membrane filters are preferably handled aseptically with tweezers. Membrane filters may be made by the user from commercially available materials or are provided in sterile packages as separate entities or as parts of kits of the invention.

Wipe devices can be used as capture elements with the culture plate devices of the present disclosure. As used herein, a "wipe device" is an article that is configured for contacting a surface to obtain a sample of microorganisms disposed thereon. Wipe devices can include porous, nonwoven materials. Nonlimiting examples of wipe materials include paper (e.g., filter paper, cellulosic membrane filters), synthetic nonwovens (e.g., nylon or polyester nonwovens), polymeric or ceramic membranes (e.g., polycarbonate membranes, zirconia membranes), and microstructured films (e.g., microchannel-containing films such as those described in U.S. Pat. No. 7,223,364, which is incorporated herein by reference in its entirety). In some embodiments, the microchannel-containing films comprise through-holes that allow the passage of liquid (and solutes or small particles) from one major surface of the film to the other major surface. Wipe devices can include chemicals (e.g., surfactants), to improve wettability, or reagents (e.g., differential stains), provided the chemical or reagents do not adversely affect the detection of acid zones adjacent the colonies of lactic acid-producing bacteria. Wipe devices in general comprise chemicals in an amount that will not substantially inhibit the growth of microorganisms under the inoculation and incubation conditions described herein. In some embodiments, the capture elements are substantially transparent or become substantially transparent when wet, allowing for the visualization of a differential reaction, such as hemolysis, through the capture element.

Suitable capture elements include a particle, or a plurality of particles. The capture elements can include a means for coupling the capture element to microorganisms. Nonlimiting examples of particles include microspheres, microbeads, and the like. Such particles can be resin particles, for example, agarose, latex, polystyrene, nylon, polyacrylamide, cellulose, polysaccharide, or a combination thereof, or inorganic particles, for example, silica, aluminum oxide, or a combination thereof. Such particles can be magnetic, paramagnetic, superparamagnetic, or non-magnetic. Such particles can be colloidal in size, for example about 100 nm to about 10 microns (µm). Nonlimiting examples of such particles include superparamagnetic polymer particles sold under the trade names DYNABEADS (Invitrogen, Inc., Carlsbad, Calif.) and BIO-ADEMBEADS (Ademtech, Pessac, France). Particle capture elements may be incorporated into other structures, such as a microporous membrane.

There are a variety of means for coupling capture element (e.g., a particle) to a microorganism. In some embodiments, the means for coupling the capture element to the microorganism can include surface molecules or properties that promote nonspecific adsorption. For example, at least a portion of the capture element can have molecules on its surface that, under the proper conditions (e.g., high pH or low pH), become positively- or negatively-charged and nonspecifically adsorb to complementary-charged molecules associated with the surface of a microorganism.

Additionally, or alternatively, at least a portion of the capture element (e.g., a polystyrene particle) can have a hydrophobic surface which nonspecifically adsorbs to hydrophobic molecules associated with the surface of a microorganism. In some embodiments, the means for coupling a capture element to a microorganism may comprise a molecule that specifically binds to a microorganism through a receptor-ligand interaction. Such specific receptor-ligand interactions are well known in the art and include interactions between, for example, antibodies and their corresponding antigens, lectins and their corresponding carbohydrate binding partner, bacteriophage proteins and their corresponding phage receptors, and the like. It should be understood that the means for coupling a particle to a microorganism can also be used in conjunction with film or nonwoven (e.g., filter) capture elements, as well as the particulate capture elements.

The thin plates of the invention are typically disinfected or sterilized before use.

Methods for Detecting Acid-producing Bacteria in a Sample

The present disclosure provides methods for detecting acid-producing bacteria in a sample. In some embodiments, the method comprises providing a thin film culture device including a cold water-soluble gelling agent, a cover sheet, a culture medium to support the growth and identification of acid-producing bacteria, a pH indicator, and a liquid sample suspected of containing acid-producing bacteria. In some embodiments, the culture device can comprise the culture medium. Additionally, or alternatively, the culture device can comprise the pH indicator.

The method further comprises inoculating the culture device with a predetermined liquid volume and thereby forming a hydrogel comprising the culture medium, the pH indicator, the optional antifungal agent, and the liquid sample. The cover sheet, if present on the thin film culture device, is separated (e.g., lifted) from the substrate when the device is inoculated with the pre-determined liquid volume. The pre-determined liquid volume can be, for example, about 1 milliliter, about 2 milliliters, about 3 milliliters, or about 5 milliliters. The pre-determined liquid volume comprises the sample, the culture medium, the pH indicator and, optionally, an aqueous diluent such as water, a saline solution, or a buffer. Components of the predetermined liquid volume (i.e., the sample, the culture medium, the pH indicator, and the optional aqueous diluent) can be added to the culture device separately or they can be added to the culture device in mixtures of two or more components (e.g., the sample can be mixed with a culture medium such as, for example, MRS broth or letheen broth and/or the sample can be mixed with a pH indicator and/or a diluent). If the components are added separately, they can be mixed briefly (e.g., stirred with a pipette tip) before the coversheet is placed over the inoculated area of the culture device.

In some embodiments, the method comprises comprising combining the sample with a diluent capable of neutralizing a chemical sanitizer. Letheen broth, for example, can be used as a diluent in methods according to the present disclosure. Letheen broth comprises lecithin and POLYSORBATE 80, which are capable of neutralizing commonly-used disinfectants such as quaternary amine compounds, for example.

The method further comprises incubating the culture device for a period of time. The incubation conditions (e.g., the incubation temperature) can affect the rate of growth of the acid-producing bacteria and may affect the types of bacteria that are detected. For example, incubation at lower temperatures (e.g., about 25° C.) can allow for the detection of psychrotrophic bacteria). Incubation at higher temperatures (e.g., about 30° C., about 32° C., about 35° C.) may facilitate faster growth of certain acid-producing bacteria.

In some embodiments, the culture device is incubated anaerobically, either in 100% carbon dioxide gas or other known methods of creating anaerobic conditions for incubation. The culture device can also be incubated under aerobic conditions.

The culture device can be incubated until evidence of acid-producing bacterial colonies is observed. Evidence of acid-producing bacterial colonies includes a detectable (i.e., by observing a detectable change in a pH indicator) acid zone within and/or adjacent a colony. In some embodiments, acid-producing bacteria can be further detected and differentiated by the presence of a gas bubble adjacent the colony. The acid zone may be observable in the absence of a visible bacterial colony. Generally, an acid zone appears in or adjacent an acid-producing bacterial colony before a gas bubble associated with the colony is observable.

In some embodiments, the culture device can be incubated for at least about 16 hours, at least about 18 hours, at least about 24 hours, or at least about 48 hours. In some embodiments, the culture device can be incubated not more than about 24 hours, not more than about 48 hours, or not more than about 72 hours. In certain preferred embodiments, the culture device is incubated about 24 hours to about 48 hours. In other preferred embodiments, the culture device is incubated about 5 days, and as long as 7 to 10 days The method further comprises detecting the presence or absence of a microorganism. Acid-producing bacteria can be detected as described herein. After a suitable incubation period, the absence of a microorganism can be detected in a culture device by the absence of observable colonies, no change in a growth indicator (e.g., the pH indicator, a chromogenic enzyme substrate, a redox indicator such as TTC) and the absence of gas bubbles associated with the metabolism of the fermentable carbohydrate in the growth medium.

An acid zone associated with a colony of microorganisms can be detected visually and/or by the use of an imaging system. For example, in a method wherein the culture medium comprises bromcresol purple as the pH indicator, the culture medium will have a purple or gray appearance at about a neutral pH. As the acid-producing bacteria grow and ferment glucose in the culture medium, the bromcresol purple indicator will appear yellow adjacent the growing bacterial colonies. For example, in a method wherein the culture medium comprises chlorophenol red as the pH indicator, the culture medium will have a red or violet appearance at about a neutral pH. As the acid-producing bacteria grow and ferment glucose in the culture medium, the chlorophenol red indicator will appear yellow adjacent the growing bacterial colonies.

Gas bubbles associated with a colony of microorganisms can be detected visually and/or by the use of an imaging system. The gas bubbles may be associated with a visible colony and/or an acid zone detectable by a change in the color of the pH indicator in a region adjacent the colony of microorganisms.

In any of the above embodiments, the method further can comprise providing an imaging system and obtaining an image of the culture device. In these embodiments, detecting the presence or absence of a microorganism comprises displaying, printing, or analyzing the image of the culture device. The imaging system comprises an imaging device and may comprise a processor. In some embodiments, the imaging device can comprise a line-scanner or an area scanner (e.g., a camera). The imaging device can include a monochromatic (e.g., black-and-white) or a polychromatic (e.g., color) scanner. Advantageously, monochromatic imaging systems can provide higher resolution images, which may improve the accuracy of the result and/or reduce the time necessary to detect the presence of microorganisms in the culture device.

In some embodiments, the imaging system further comprises an illumination system. The illumination system may include at least one source of broad-spectrum visible light (e.g., a "white" light). In some embodiments, the illumination system may include at least one source of narrow-spectrum visible light (e.g., a light-emitting diode that emits a relatively narrow bandwidth of visible light such as, for example, red, green, or blue light). In certain embodiments, the illumination system may include a source of narrow-spectrum visible light (e.g., a light-emitting diode) with a light emission peak at about 525 nm.

The image can be obtained from light reflected by the hydrogel in the culture device or the image can be obtained from light transmitted through the hydrogel in the culture device. Suitable imaging systems and corresponding illumination systems are described, for example, in International Patent Publication No. WO 2005/024047 and U.S. Patent Application Publication Nos. US 2004/0101954 and US 2004/0102903, each of which is incorporated herein by reference in its entirety. Non-limiting examples of suitable imaging systems include PETRIFILM Plate Reader (PPR), available from 3M Company (St. Paul, Minn.), the PETRISCAN Colony Counter available from Spiral Biotech (Norwood, Mass.), and PROTOCOL and ACOLYTE plate scanners available from Symbiosis (Cambridge, U.K.)

In some embodiments, obtaining an image comprises obtaining a wavelength-biased image. For example, the imaging system can include a bias filter that biases the light collected by the imaging device. Filter elements are known in the art and include both "cut-off" filters (i.e., filters that allow the passage of light wavelengths either above or below a certain specified wavelength) and "band-pass" filters (i.e., filters that allow the passage of light wavelengths between certain specified upper and lower limits). A bias filter can be positioned between the illumination source and the culture device. Alternatively or additionally, a bias filter can be positioned between the culture device and the imaging device.

In certain preferred embodiments, obtaining an image comprises obtaining an image using a bias filter that selectively allows the passage of red wavelengths. In some embodiments, obtaining an image comprises using a bias filter that selectively allows the passage of wavelengths from about 500 nm to about 550 nm.

Figure 5:
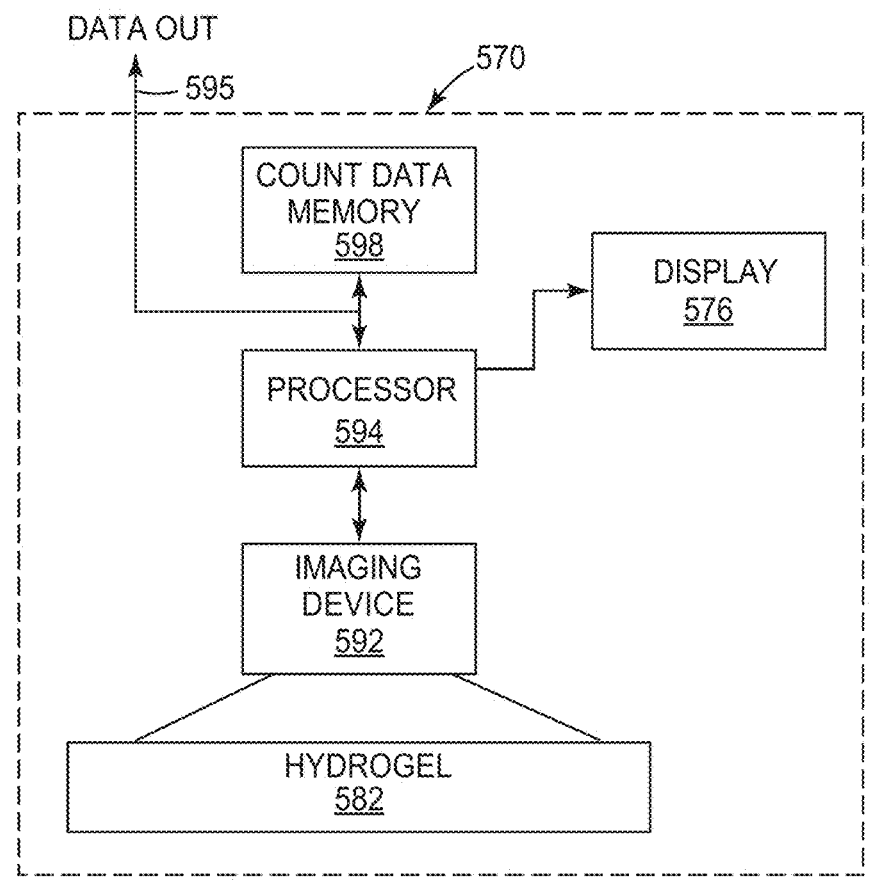
FIG. 5 is a block diagram of one embodiment of a detection system according to the present disclosure.

FIG. 5 is a block diagram illustrating internal operation of an imaging system 570. As illustrated in FIG. 5, a culture device 582 is positioned in a focal plane (e.g., on a platform, not shown) within imaging system. In accordance with the invention, imaging device 592 may include multi-color illumination systems (not shown) for front and/or back illumination of culture device 582, as well as a monochromatic line or area scanner that captures an image of the culture device 582. In some embodiments, for example, imaging device 592 may take the form of a two-dimensional, monochromatic camera.

In general, imaging device 592 captures images of culture device 582, or at least a portion thereof, during illumination of the culture device with one or more different illumination colors. In some embodiments, multiple images of the same culture device 582 can be generated with various illumination durations or intensities and one or more of the multiple images can be selected for analysis. In some embodiments, selective illumination of a first side and a second side of the culture device 582 can be used to generate multiple images of the culture device and one or more of the images can be selected for analysis. Selection of an image for analysis can be based on, for example, the color contrast and/or object resolution properties of the individual images. Processes for determining the color contrast and object resolution properties of an image are known in the art and are disclosed in, for example, U.S. Pat. No. 6,243,286, which is incorporated herein by reference in its entirety.

A processor 594 controls the operation of imaging device 592. Also shown in FIG. 5 is optional display 576, which can receive an image from the processor 594 for visual review by an operator. In operation, processor 594 controls imaging device 592 to illuminate the culture device 582 and obtain an image. Processor 594 receives image data representing the scanned image from imaging device 592. In some embodiments, processor 594 can select an image, from multiple images, for analysis and/or display. Processor 594 analyzes at least one image of culture device 582 and may produce an analytical result, such as a count of colonies of acid-producing bacteria or a determination of the presence or absence of acid-producing bacteria in a sample. The analytical result (e.g., a qualitative or quantitative result) can be displayed on display 576, stored in optional data storage memory 598, or retrieved by a host computer (not shown) via optional communication port 595

The method further comprises detecting acid-producing bacteria in the culture device. Detecting acid-producing bacteria in the culture device comprises analyzing the image of the culture device. Glucose in the culture medium is fermented by acid-producing bacteria into byproducts that include acid. Because the diffusion of acid away from the microorganisms is limited by the hydrogel, the production of acid by a colony of acid-producing bacteria results in the accumulation of acid adjacent the colony. This accumulation of acid can cause a detectable change (e.g., a color change) of the pH indicator in the culture medium adjacent the colony. Thus, analyzing the image of the culture device can comprise analyzing the image for zones in the culture medium that have a different color composition than at least one other portion of the hydrogel. The color change will be dependent upon the pH indicator in the culture medium. For example, bromcresol purple will appear purple in the culture medium with yellow zones adjacent the colonies that are producing lactic acid. Chlorophenol red will appear red to violet in the culture medium with yellow zones adjacent the colonies that are producing lactic acid. In some embodiments, analyzing the image of the culture device can comprise comparing the color of the culture medium in one or more areas (or the entire area) of the inoculated culture device to another image of a corresponding culture device inoculated with, for example, sterile water (i.e., a negative control).

Analyzing the image of the culture device can comprise using a system to detect color and/or varying shades of a color (e.g., red, green, blue, gray) in an image. Suitable image analysis systems include the image analysis systems described in, for example, U.S. Pat. Nos. 5,448,652; 6,243, 486; and 6,153,400; each of which is incorporated herein by reference in its entirety.

In certain embodiments, analyzing the image of the culture device comprises analyzing selected wavelengths of the image. In some embodiments, the image may be a color image collected by illuminating the culture device with a source of broad-spectrum visible light (e.g., a "white" light). In some embodiments, the image may be a color image collected by illuminating the culture device with a plurality of sources of relatively narrow-spectrum visible light (e.g., a combination of light-emitting diodes that each emits a relatively narrow bandwidth of visible light such as, for example, red, green, or blue light). In some embodiments, the image may be a composite image made by combining two or more images collected while illuminating the culture device with two or more different sources of relatively narrow-spectrum visible light (e.g., red, green, or blue light). In some embodiments, the image may be an image collected while illuminating the culture device with a source of relatively narrow-spectrum visible light (e.g., green light). In these embodiments, certain wavelengths of the image can be selected for displaying or printing an image and/or image analysis.

In some embodiments (e.g., wherein the color of the pH indicator ranges from red to yellow), the wavelengths selected for analyzing the image can be wavelengths in the green color range (e.g., wavelengths about 500 nm to about 550 nm). In some embodiments, the wavelengths selected for analysis are wavelengths about 520 nm to about 530 nm. In some embodiments, the wavelength selected for analysis is about 525 nm.

The wavelengths can be selected, for example, by using a computer program that electronically selects a predetermined range of wavelengths in the image for display, printing, and/or analysis. For example, a predetermined green wavelength or range of green wavelengths may be particularly suitable to display, print, or analyze an image of a yellow-colored zone adjacent a colony of lactic acid bacteria growing in a red-colored culture medium (e.g., a culture medium comprising chlorophenol red). Any suitable computer program can be used to select a predetermined range of wavelengths in an image. Non-limiting examples of suitable computer programs include PHOTOSHOP CS4 software, available from Adobe Systems, Inc. (San Jose, Calif.) and IMAGE-PRO Plus software, available from Media Cybernetics (Silver Springs, Md.).

In certain embodiments, wherein the image of the culture device has been obtained and/or analyzed in a manner that biases the collection in the image of green wavelengths either transmitted through and/or reflected by the hydrogel in the culture device, the contrast between the pH indicator (e.g., the red-colored chlorophenol red) in the culture medium and the acid zone (e.g., the yellow-colored chlorophenol red) adjacent the bacterial colonies is significantly enhanced. Thus, in these embodiments, acid-producing bacteria are detectable at an earlier time than in comparable methods that do not bias the wavelengths of the image that is collected.

Kits of the Invention

Kits provided by the present invention include a culture device comprising a cold water-soluble gelling agent, a culture medium to support the growth and identification of acid-producing bacteria, and a pH indicator. In some embodiments, the culture device can comprise the culture medium to support the growth and identification of acid-producing bacteria and/or the pH indicator.

In some embodiments, the kit comprises a dehydrated culture medium to support the growth and identification of acid-producing bacteria. In some embodiments, the dehydrated culture medium comprises a pH indicator.

In some embodiments, the kit comprises a liquid culture medium to support the growth and identification of acid-producing bacteria. In some embodiments, the liquid culture medium comprises a pH indicator.

Kits of the present invention may further comprise a sample preparation accessory to assist in the preparation and/or inoculation of the sample. Non-limiting examples of sample preparation accessories include a diluent, a buffer, a sample acquisition device (e.g., a swab, a sponge, a spatula), and a pipette.

The invention will be further illustrated by reference to the following non-limiting Examples. All parts and percentages are expressed as parts by weight unless otherwise indicated.

EXAMPLES

Example 1

Detection of Lactic Acid Bacteria Isolated from Processed Meat Samples Using a Bromcresol Purple pH Indicator 3M PETRIFILM Aerobic Count plates were obtained from 3M Company (St. Paul, Minn.). DIFCO MRS broth was obtained from BD-Diagnostic Systems (Sparks, Md.).

Four strains of lactic acid-producing bacteria were isolated from processed meats. Two of the cultures were identified as *Leuconostoc mesenteroides* and *Weissella viridescens, Lactococcus lactis* subspecies *lactis* and *Streptococcus oralis*.

Bromcresol purple (BCP) pH indicators was obtained from Eastman Kodak (Rochester, N.Y.). Chlorophenol red (CPR) (CAS NO. 4430-20-0) was obtained from Sigma-Aldrich (St. Louis, Mo.). The pH indicators were individually added to MRS broth to obtainfinal concentrations of BCP or CPR of 0.5 mM. After dissolving the pH indicator, the solutions were filter-sterilized.

Bacterial cultures were prepared by inoculating pure cultures into tryptic soy broth or MRS broth. The inoculated broth was incubated overnight at 25° C. The overnight cultures were diluted in the MRS broth (containing bromcresol purple) to obtain a suspension of approximately 10-100 colony-forming units (CFU) per milliliter. One milliliter of each diluted bacterial suspension was used to inoculate PETRIFILM Aerobic Count plates according to the manufacturer's instructions. Inoculated plates were incubated at temperatures at 25°, 30° and 32° C., respectively. The plates were visually inspected for signs of bacterial growth. The results are shown in Table 3.

Example 2

Detection of Lactic Acid Bacteria Isolated from Processed Meat Samples Using a Chlorophenol Red pH Indicator A concentrated solution of sterile chlorophenol red was added to the MRS diluent as described in Example 2. A concentrated solution of sterile dipotassium phosphate (pH 7.0+/−0.2) was added to the MRS diluent to provide an additional 28 mM phosphate buffer in the diluent. Lactic acid bacterial cultures were prepared and diluted into the MRS/chlorophenol red solution as described in Example 1 with the exception that *S. oralis* was not tested in this experiment. The diluted bacterial suspension was used to inoculate PETRIFILM Aerobic Count Plates as described in Example 1. The plates were incubated at 30° C. and the plates were visually inspected for signs of bacterial growth. The results are shown in Table 3.

Example 3

Detection of Lactic Acid Bacteria Isolated from Processed Meat Samples Using a Chlorophenol Red pH Indicator A concentrated solution of sterile chlorophenol red was added to the MRS diluent as described in Example 2. A concentrated solution of sterile dipotassium phosphate (pH 7.0+/−0.2) was added to the MRS diluent to provide and additional 28 mM phosphate buffer in the diluent. Lactic acid bacterial cultures were prepared and diluted into the MRS/chlorophenol red solution as described in Example 1 with the exception that *S. oralis* was not tested in this experiment. The diluted bacterial suspension was used to inoculate PETRIFILM Aerobic Count Plates as described in Example 1. The plates were incubated at 30° C. and the plates were visually inspected for signs of bacterial growth. The results are shown in Table 3.

TABLE 3

Detection of lactic acid bacteria in a thin film culture device.

| Example | pH Indicator | Buffer Addition | Incubation Temperature | Incubation Time | Observations |
|---|---|---|---|---|---|
| 1 | Bromcresol Purple: 0.02 g/l or 0.04 g/l | None | 25 C 30 C | 18-24 hr | *L. lactis* subspecies *lactis*: Colonies with acid zones. No gas bubbles. *S. oralis*: ND Leuconostoc: ND Weissella: Acid zones without visible colonies. No gas bubbles. |
| | | | | 40-72 hr | *L. lactis* subspecies *lactis*: Colonies with acid zones. No gas bubbles. *S. oralis*: Acid zones. No visible colonies or gas bubbles. Leuconostoc: Acid zones. No visible colonies or gas bubbles. Weissella: Acid zones and gas bubbles. Pale colonies. |

TABLE 3-continued

Detection of lactic acid bacteria in a thin film culture device.

| Example | pH Indicator | Buffer Addition | Incubation Temperature | Incubation Time | Observations |
|---|---|---|---|---|---|
| 2 | Chlorophenol Red: 0.21 g/l | None | 30 C | 18-24 hr | Acid zones were visible for all three microorganisms tested. |
|  |  |  |  | 40-72 hr | *L. lactis* subspecies *lactis*: Colonies with acid zones and gas bubbles. Weissella: Colonies with acid zones and gas bubbles. Leuconostoc: Acid zones and gas bubbles. No visible colonies. |
| 3 | Chlorophenol Red: 0.21 g/l | 28 mM | 30 C | 18-24 hr | Acid zones visible with all three strains. |
|  |  |  |  | 40-72 hr | *L. lactis* subspecies *lactis*: Colonies with acid zones and gas bubbles. Weissella: Colonies with acid zones and gas bubbles. Leuconostoc: Acid zones. No visible colonies. |

ND = no data collected.

Example 4

Image Analysis of Petrifilm Plate Images

An overnight culture of *Weissella viridescens* was prepared and diluted into individual MRS broths containing bromcresol purple or chlorophenol red, as described in Example 2. The diluted suspensions were used to inoculate 3M PETRIFILM Aerobic Count plates. After inoculation, the plates were incubated at 30 C for 48 hours.

After incubation, the plates were imaged using a Petrifilm Plate Reader (PPR) that was set up to scan a standard PETRIFILM Aerobic Count Plate. The bitmap images generated by the PPR were imported into Adobe PhotoShop® software (Adobe Systems, San Jose, Calif.). The software was used to view the green channel of the image to visualize yellow zones adjacent the colonies due to lactic acid associated with the colony.

The red, green and blue images were exported into IMAGE-PRO Plus version 6.3.0.512 software and the respective color images were converted to grayscale bitmap images. The software was used to select the pixels on a diagonal line passing through the light-colored zone on the red image. The line profile below each respective image shows the pixel intensity for each pixel on the diagonal line shown in the image.

Figure 6:
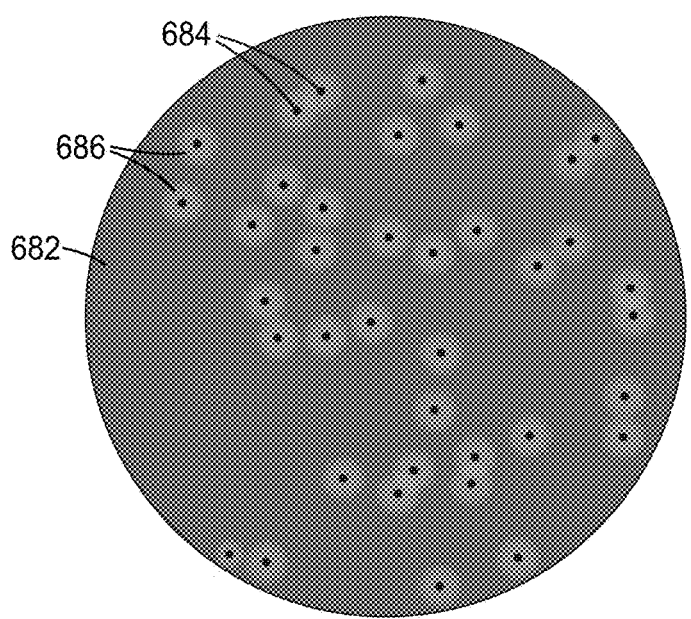
FIG. 6 is representation of a black-and-white image of the growth area of a PETRIFILM plate illuminated with green light-emitting diodes.

The bitmap images from a plate containing bromcresol purple are shown in FIG. 6. The sharp peak in the red channel image corresponds to the red-colored colony in the center of the acid zone. The broad peak in the green channel image corresponds to the yellow-colored pH indicator (acid) zone adjacent the bacterial colonies. The sharp troughs in the blue channel image correspond to the yellow-colored grid lines in the thin film culture device.

The bitmap images from a plate containing chlorophenol red are shown in FIG. 7. There is no detectable peak in the red channel image. The broad peak in the green channel corresponds to the yellow-colored pH indicator (acid) zone adjacent the bacterial colonies. The sharp troughs in the blue channel correspond to the yellow-colored grid lines in the thin film culture device.

Example 5

Detection of Lactic Acid Bacteria in Thin Film Culture Devices Using Chlorophenol Red, Bromcresol Green, and Bromphenol Blue Indicator Dyes Bromocresol Green sodium salt (CAS No. 62625-32-5), Bromphenol Blue sodium salt (CAS No 34725-61-6), and Chlorophenol Red (CAS NO. 4430-20-0) were obtained from Sigma-Aldrich.

A diluent stock solution containing the components of MRS broth and Letheen broth was prepared according to the formula in Table 4. The stock solution was split into four aliquots. Chlorophenol red, bromcresol green, and bromphenol blue indicator dye was added to a concentration of 0.5 mM to one of the four aliquots. The fourth aliquot did not receive any pH indicator dye. The aliquot were separately filter-sterilized.

TABLE 4

Diluent Stock Solution. Ingredients were added to the water and stirred until dissolved.

| Ingredient | Amount (grams) |
|---|---|
| Proteose Peptone No. 3 | 10 |
| Bacto Peptamin | 10 |
| Yeast Extract | 5 |
| Dextrose | 20 |
| Beef Extract | 15 |
| $K_2HPO_4$ | 2 |
| Polysorbate 80 | 6.0 |
| Ammonium citrate | 2.0 |
| Sodium acetate | 5.0 |
| Magnesium sulfate | 0.1 |
| Manganese sulfate | 0.05 |
| Lethicin | 0.7 |
| Sodium Chloride | 5 |
| Deionized Water | 1000 |

Overnight cultures of *Lactococcus lactis* subspecies *lactis* and *Leuconostoc mesenteroides* were prepared as described in Example 1. The overnight cultures were diluted 1:10,000 in Butterfield's diluent. The diluted cultures were subsequently serially diluted in the diluent stock solution (Table 4) to a concentration of about 10-100 CFU/mL. The final suspensions were used to inoculate duplicate PETRIFILM Aerobic Plate Count Plates according to the manufacturer's instructions. One set of plates was incubated at 25° C. and one set was incubated at 32° C. The plates were imaged with a Petrifilm Plate Reader and the images were observed after 24 hours, 48 hours, and 72 hours of incubation. The results are summarized in Table 5. Colonies, when visible, appeared red due to the TTC indicator in the plate. Yellow zones typically appeared as a halo around the colonies and were at least 2-3 mm in diameter after 24 hours of incubation. The zones appeared larger after further incubation (e.g., approximately 5-10 mm in diameter after 48 hours and >10 mm diameter after 72 hours). Gas bubbles, when present, were adjacent visible colonies and/or were located in the yellow zones. The number of gas bubbles was typically greater with increased incubation time.

TABLE 5

Colony appearance on thin film culture devices containing pH indicators.

| Culture | pH Indicator | Temperature | 24-hour Results | 48-hour Results | 72-hour Results |
|---|---|---|---|---|---|
| L. lactis subspecies lactis | Chlorophenol Red | 25° C. | ND | ND | ND |
| | | 32° C. | Colonies; yellow zones | Colonies; yellow zones | Colonies; large yellow zones, gas |
| | Bromocresol Green | 25° C. | No visible colonies, acid zones or gas bubbles | Pale colonies, pale yellow zones, no gas bubbles | Pale colonies, pale yellow zones, small gas bubbles |
| | | 32° C. | Pale yellow zones | Pale colonies, pale yellow zones, small gas bubbles | Pale colonies, pale yellow zones, small gas bubbles |
| | Bromphenol Blue | 25° C. | No visible colonies, acid zones or gas bubbles | Pale colonies | Colonies, gas |
| | | 32° C. | No visible colonies, acid zones or gas bubbles | pale colonies | Colonies, gas |
| L. mesenteroides | Chlorophenol Red | 25° C. | ND | ND | ND |
| | | 32° C. | Yellow zones | Yellow zones, gas | Colonies; large yellow zones, gas |
| | Bromocresol Green | 25° C. | Colonies, yellow zones | Pale colonies, pale yellow zones, small gas bubbles | Pale colonies, yellow zones, small gas bubbles |
| | | 32° C. | Colonies, yellow zones | Pale colonies, yellow zones, small gas bubbles | Pale colonies, yellow zones, small gas bubbles |
| | Bromphenol Blue | 25° C. | No visible colonies, acid zones or gas bubbles | No visible colonies, acid zones or gas bubbles | Gas bubbles only (no colonies or acid zones) |
| | | 32° C. | ND | Pale colonies, gas bubbles | Pale colonies, gas bubbles |

"ND" means no data for the time point.

Example 6

Preparation of MRS Media for Thin Film Culture Device (Plates I-VI, IX)

Media compositions shown in Table 6 were prepared according to the following procedure and then used to make thin film plates. The broth media was prepared by dissolving sodium pyruvate (obtained from Sigma-Aldrich (St. Louis, Mo.)) with reverse osmosis treated water (RO water), and then adding MRS Broth Nutrients (Remel R454064 obtained from Thermo Fisher Scientific, (Lenexa, Kans.)) until dispersed. The pH of the prepared media was about 6.6 and was adjusted using hydrochloric acid (HCl) at a concentration of 2.5 N or 1.0 N. Guar gum (M150 guar MEYPROGAT gum, Meyhall Chemical AG) was slowly added to the mixture while stirring and then heated to a temperature of 80° C., and then mixed for approximately another 15 minutes without heat. The mixture was cooled and refrigerated.

Addition of Chlorophenol Red

When used, Chlorophenol Red ((CAS NO. 4430-20-0) obtained from Sigma-Aldrich (St. Louis, Mo.) was dissolved in RO water before adding the remaining ingredients.

Addition of Cycloheximide

A solution of cycloheximide was prepared by dissolving cycloheximide (obtained from Sigma-Aldrich, St. Louis Mo.) in sterile RO water. The solution was added to the cooled broth media and mixed about 15 minutes.

Addition of Nystatin

A solution of Nystatin was prepared by dissolving the nystatin in methanol and sterile water was added the cooled broth media and mixed for about 15 minutes.

TABLE 6

Media Compositions Used for Thin Film Plate Assemblies

| Media Composition | Plate I | Plate II | Plate III | Plate IV | Plate V | Plate VI | Plate IX |
|---|---|---|---|---|---|---|---|
| RO Water - liter | 1.0 | 1.5 | 1.5 | 1.0 | 1.0 | 1.0 | 1.0 |
| Chlorophenol Red - grams | — | — | 0.3 | 0.2 | 0.2 | 0.4 | 0.2 |
| Sodium Pyruvate - grams | 6.0 | 9.0 | 9.0 | 6.0 | 6.0 | 6.0 | 6.0 |
| MRS Nutrients - grams | 104 | 156 | 156 | 104 | 104 | 104 | 104 |
| HCL - mL (conc) | 8 (1N) | 10 (2.5N) | 4 (2.5N) | 2 | — | — | 2 |
| Guar - grams | 11 | 16.5 | 16.5 | 11.0 | 11.0 | 11.0 | 11.0 |
| Broth media pH* | 6.6 | 6.6 | 6.6 | 6.6 | 6.6 | 6.4 | 6.6 |
| Adjusted pH | 5.8 | 5.8 | 5.8 | 6.3-6.4 | — | — | 5.8 |
| Additive Solutions | | | | | | | |
| Cycloheximide - (grams) | — | 0.03 | 0.03 | — | — | — | 0.02 |
| Nystatin | — | — | — | 2500 Units | — | — | — |
| Water - mL | — | 30 | 30 | 27 | — | — | 27 |
| Methanol - mL | — | — | — | 3 | — | — | 3 |

*pH of broth as prepared

Thin Film Culture Device Assembly (Plates I-IX)

Thin film culture plates (FIG. 1) were prepared using the media compositions described above for each of the plates. A water-proof adhesive coated paper substrate printed with a grid was coated on the gridline side with the media to a width of about 7.5 inches (19.1 cm) using a knife coater to a target coating weight of about 0.46 g/155 cm$^2$) The coated substrate was dried in an oven set at 210° F. (98.9° C.) for about 4 minutes.

The coated substrate was cut into a sheet approximately 16 inches (10.6 cm long. A 0.46 mm thick sheet of closed cell polystyrene foam was laminated to an adhesive transfer tape on a liner. The adhesive coated foam sheet was die-cut so that it had ten 2-inch (5.1 cm) diameter circular cut-outs centered within 3-inch (7.6 cm) by 3-inch (7.6 cm) rectangular areas on the sheet. The release liner was removed and the foam was laminated to the broth coated side of the substrate. A top film prepared as described in Example 12 of U.S. Pat. No. 4,565,783, which is incorporated in its entirety herein by reference, using ethylene oxide treated guar, was used as a cover film and attached to the substrate sheet with a hinge tape. The composite was then cut into 3-inch (7.6 cm) by 4-inch (10.2 cm) rectangular plates with the cut out centered within a 7.6 cm square from one edge of the plate.

Plate VII was prepared in a similar manner except that the water-proof paper was used without a coating of media so that the foam die-cut sheet was laminated directly to the paper.

Plate VIII was prepared by laminating a 3M™ Petrifilm™ Aerobic Count Plate to the top film described above.

Preparation of Universal Beer Agar Media

A media compositon was prepared by mixing the components in the amounts listed in Table 7 with 375 milliliters of deionized until dispersed and then heated to a temperature of 80° C. The beer was added and mixed for about 15 minutes and the media was refrigerated overnight.

Example 7

Detection of Lactic Acid Bacteria from Beer Samples in the Presence of Chlorophenol Red Eleven strains of lactic acid-producing bacteria (LAB) were obtained from commercial breweries and classified using a VITEK biochemical processor Biomerieux). The eleven strains were classified as *Lactobacillus brevis* (2 strains), *Lactobacillus plantarum*, *Pediococcus damnosus* (3 strains), *Pediococcus acidilactici* (2 strains), *Pediococcus dextrinicus, Lactobacillus delbrueckii*, and *Lactobacillus paracasei* according to standard identification proceduers.

A pH indicator solution was prepared by dissolving 0.0798 grams of Chlorophenol red sodium salt ((CPR) CAS NO. 123333-64-2 obtained from Sigma-Aldrich (St. Louis, Mo.)) in 198.0 ml of sterile Butterfields Buffer (EdgeBiologicals; Memphis, Tenn.). Two-fold serial dilutions were performed to obtain final concentrations of 0 µg/ml (no CPR was added), 50 µg/ml (0.1 mM), 100 µg/ml (0.2 mM), 200 µg/ml (0.4 mM) and 400 µg/ml (0.8 mM) in CPR buffer.

Bacterial cultures of each strain of LAB were prepared by inoculating pure cultures into sterile deMan, Rogosa and Sharpe broth ((MRS, Product number R454064 obtained from Remel (Lenexa, Kans.)). The MRS broth was prepared according to the manufacturer's guidelines. The inoculated broth was incubated for 3 days at 28° C. in a 99.9% carbon dioxide incubator. The cultures were diluted in the CPR buffer to obtain suspensions containing approximately 10-500 colony-forming units (CFU). One milliliter of each diluted culture was used to inoculate thin film plates (Plate I). Additionally, one-tenth milliliter of the bacterial dilution containing 100-5000 CFU was used to inoculate agar plates (Universal Beer Agar plates (obtained from AlphaBioSciences, Baltimore, Md.). The thin film plates and agar plates were incubated for 5 days at 28° C. in a 99.9% carbon dioxide incubator. The plates were visually inspected for signs of bacterial growth after 2 days and 5 days.

The isolates recovered at 2 days and 5 days are shown in Table 8.

TABLE 7

Universal Beer Agar Media Composition

| Component | Amount | Company | Catalog No. | CAS No. |
|---|---|---|---|---|
| Dipotassium phosphate | 0.158 g | JT Baker | 4012-01 | 7758-11-4 |
| Monopotassium phosphate | 0.155 g | JT Baker | 3246-01 | 7778-77-0 |
| Magnesium Sulfate | 0.062 g | Fisher | M63-500 | 10034-99-8 |
| Manganese Sulfate | 100 µL of soln (0.2997 g/10 ml H2O) | Aldrich | 04723HN MQ | 10034-96-5 |
| Sodium Chloride | 100 µL of soln (0.3036 g/10 ml H2O) | EM Science | SX0420-1 | 7647-14-5 |
| Ferrous Sulfate | 100 µL of soln (0.2980 g/10 ml H2O) | Mallinckrodt | 5056 | 7720-78-7 |
| Dextrose | 8.05 g | Sigma | G-6152 | 492-62-6 |
| Peptonized Milk | 7.56 g | Oxoid | LP0032 | |
| Yeast Extract | 2.99 g | Difco | 210929 | |
| Tomato Juice Powder | 6.06 g | Blue California | | |
| Guar Gum | 4.98 g | | | |
| Beer | 125 ml | | | |
| dH2O | 375 ml | | | |

TABLE 8

Bacterial growth with varying chlorophenol red concentrations

| | 2 Days | | | | | | 5 Days | | | | | |
|---|---|---|---|---|---|---|---|---|---|---|---|---|
| | Agar | Plate 1 | | | | | Agar | Plate 1 | | | | |
| | | | | CPR Conc-µg/ml | | | | | | | | |
| | 0 | 0 | 50 | 100 | 200 | 400 | 0 | 0 | 50 | 100 | 200 | 400 |
| P. damonosus (1) | − | − | − | − | − | − | + | + | + | + | + | + |
| P. damonosus (2) | + | + | + | + | + | + | + | + | + | + | + | + |
| P. damonosus (3) | − | − | − | − | − | − | + | + | + | + | + | + |
| P. dextrinicus | − | − | − | − | − | − | − | + | − | − | − | − |
| L. delbrueckii | + | − | − | − | − | − | + | + | + | + | + | + |
| L. brevis (1) | + | + | + | + | + | + | + | + | + | + | + | + |
| L. brevis (2) | + | + | + | + | + | + | + | + | + | + | + | + |
| L. plantarum | + | + | + | + | + | + | + | + | + | + | + | + |
| L. paracasei | + | + | + | + | + | + | + | + | + | + | + | + |
| L. acidilactici (1) | + | + | + | + | + | + | + | + | + | + | + | + |
| L. acidilactici (2) | + | + | + | + | + | + | + | + | + | + | + | + |

+ indicates growth;
− indicates no growth

Example 8

Detection of Lactic Acid Bacteria in Beer Samples in MRS Media

MRS broth (Remel (Lenexa, Kans.)) was prepared at concentrations of 52 grams per liter, 70 grams per liter, 105 grams per liter, and 140 grams per liter. The broth was steam sterilized according to the manufacturer's guidelines.

Cultures of *Lactobacillus brevis* (3 strains) and *Pediococcus damnosus* were prepared as described in Example 7. The cultures were serially diluted in the prepared MRS broths to obtain suspensions containing approximately 10-200 colony-forming units (CFU) per milliliter. One milliliter of each of the bacterial dilutions was inoculated onto Plate VII. The plates were incubated at 28° C. for 4 days in a 99.9% carbon dioxide incubator. The plates were checked for growth after 3 days and 4 days. At 3 days, two of the three *Lactobacillus brevis* bacteria strains were growing on both types of plates. The other *Lactobacillus brevis* and *Pediococcus damnosus* were not recovered by 4 days.

Example 9

Detection of Lactic Acid Bacteria Filtered from Artificially Spiked Beer Samples A culture of *Lactobacillus brevis* was prepared as described in Example 1. The culture was diluted in beer to obtain suspensions that contained approximately 1-10 CFU per milliliter. This was accomplished by combining 0.01 ml culture with 99 ml sterile Butterfields Buffer (Dilution A). Then 0.0355 ml of Dilution A was combined with 355 ml beer (Dilution B). A 35 ml aliquot of Dilution B was filtered through a 0.45 µm mixed cellulose ester membrane (Product No. MSP000814 available from Millipore (Billerica, Mass.)). A second 35 ml sample of Dilution B was filtered through a 0.45 µm white filter Pall 60043 PES available from PALL Corporation (Port Washington, N.Y.)). A third 35 ml sample of Dilution B was filtered through a 0.45 µm PES filter (Pall 66585 PES available from PALL Corporation (Port Washington, N.Y.)).

Four plates were prepared for each filter type as follows:
UBA—Universal Beer Agar Plate, prepared according to the manufacturer's guidelines (AlphaBiosciences (Baltimore, Md.))
Plate VIII was hydrated with 1.0 ml sterile MRS broth (Remel) prepared according to the manufacturer's guidelines.
Plate I was hydrated with 1.0 ml sterile Butterfields Buffer (EdgeBiologicals (Memphis, Tenn.))
Plate I was hydrated ml Butterfields buffer containing 0.2 mg per milliliter CPR.

The plates were left at ambient temperature for 30-60 minutes after hydrating to allow the gel to solidify. The top films were rolled back from the bottom film so the gel adhered to the top films. The filters were placed right side up in the foam dam area or in the center of plate when no foam dam was used. The top film was rolled back down onto the plate and smoothed using light finger pressure. For the agar plate, the filter was placed right side up on the agar surface. The plates were incubated at 28° C. for 5 days in a 99.9% CO2 incubator. The plates were checked for growth at 3 days and 5 days. At 3 days, the *L. brevis* bacteria grew on both the Petrifilm plates and the Universal Beer agar plates. Results are summarized in Table 9.

TABLE 9

Bacteria recovery from filters

| Plate Type | No Filter Control | Pall Filter (white) | Pall Filter (black) | Millipore Filter (black) |
|---|---|---|---|---|
| UBA | Clear/yellow media; no CFU | Small, white CFU | Small, white CFU | Small, white CFU |
| Plate VIII | Clear media; No CFU | Pink, small CFU | Pink, small CFU | White, light pink, small CFU |

TABLE 9-continued

| | Bacteria recovery from filters | | |
|---|---|---|---|
| Plate Type | No Filter Control | Pall Filter (white) | Pall Filter (black) | Millipore Filter (black) |
| Plate I | Clear media; No CFU | Pink, small CFU | Dark pink/purple, small CFU | Dark pink/purple, small CFU |
| Plate VI | Purple media; no CFU | Pink, small CFU with yellow acid zone | Dark pink/purple, small CFU with hazy yellow zone | Dark pink/purple, small CFU with hazy yellow zone |

Plates were prepared as described above using the mixed cellulose ester membrane filters in a UBA Plate and Plate I except the filters were placed upside down and right side up in Plate I and UBA. A second set of identical filters was placed upside down on the plate. Results are shown in Table 10.

TABLE 10

| Bacterial growth and filter orientation | | |
|---|---|---|
| Filter orientation | Filter Right Side Up | Filter Upside Down |
| UBA | About 25 colonies | About 25 colonies |
| Plate I | About 50 colonies | About 30 colonies |

Example 10

Bacteria Growth in MRS Media over pH Range

Four preparations of MRS media (R454064 available from Remel (Lenexa, Kans.)) were prepared. The media was prepared according to the manufacturer's guidelines with the following exceptions. In addition to the MRS nutrient media, sodium pyruvate was added to the nutrient mixture. Additionally prior to autoclaving the media, the pH was taken using a pH meter. The pH of the media was adjusted to 3.5, 4.5, 5.5 or 6.5 using 1N HCl or 1N NaOH. The media was autoclaved according to the manufacturer's guidelines. After cooling the media to ambient temp, an aliquot of the media was aseptically removed from the sample and the pH was taken again with a pH meter. The pH did not change significantly (+/−0.1 pH units) during the autoclaving process.

Overnight bacterial cultures of *L. brevis* and *P. damnosus* (2 strains) were prepared as described in Example 7. The cultures were serially diluted in the 4 pH adjusted MRS broths to obtain 25-250 cfu/ml. One ml of each diluted culture was inoculated onto Plate VII. Test results are shown in Table 11.

TABLE 11

| Bacterial Growth and pH | | | | | |
|---|---|---|---|---|---|
| | Bacteria | pH 3.5 | pH 4.5 | pH 5.5 | pH 6.5 |
| Day 1 | *L. brevis* | --- | --- | --- | --- |
| | *P. damnosus* - strain 1 | --- | --- | --- | --- |
| | *P. damnosus* - strain 2 | --- | --- | --- | --- |
| Day 4 | *L. brevis* | --- | --- | + | + |
| | *P. damnosus* - strain 1 | --- | --- | + | --- |
| | *P. damnosus* - strain 2 | --- | --- | --- | --- |
| Day 6 | *L. brevis* | --- | + | + | + |
| | *P. damnosus* - strain 1 | --- | + | + | --- |
| | *P. damnosus* - strain 2 | --- | + | + | --- |
| Day 7 | *L. brevis* | --- | + | + | + |
| | *P. damnosus* - strain 1 | --- | + | + | + |
| | *P. damnosus* - strain 2 | --- | + | + | + |

+ Positive growth
--- Negative growth

Example 11

Detection of Lactic Acid Bacteria with Yeast and Cycloheximide

Overnight cultures of *Lactobacillus brevis* in MRS broth and *Saccharomyces cerevisiae* in yeast peptone dextrose (YPD) broth were prepared as described in Example 7. The cultures were serially diluted to obtain suspensions, each containing approximately 100 cfu/ml of the individual species (either *L. brevis* or *S. cerevisiae*). A third suspension was prepared containing 100 cfu/mL total of both species. A second set of 3 suspensions was prepared in the same manner (only *L. brevis*, only *S. cerevisiae*, and both organisms) except that each final solution also contained 100 ppm (10 mg/mL) cycloheximide ((CAS No. 66-81-9), sold under the tradename Actidione and obtained from Sigma (Fluka). The cycloheximide was added by using a stock solution of cycloheximide prepared by dissolving 100 ppm of cycloheximide to Butterfield's Buffer and sterile filtering the solution through a 0.2 μm filter. The stock solution was added to the diluent buffer.

One milliliter of each of the bacterial suspensions was used to inoculate Plate I. The plates were incubated at 28° C. for 48 hr in an incubator having an environment of 99.9% carbon dioxide. The plates were inspected for growth of colonies and results are summarized in Table 12. Growth indicates the presence of colonies. Cyloheximide concentrations of 0, 5, 10, 40, and 100 ppm prepared in the same manner described above were tested and all yielded similar results with two distinct colony morphologies appearing on plates with no cycloheximide, one distinct colony morphology on the plates with cycloheximide, and no growth on the plate with only *S. cerevisiae*.

TABLE 12

| Colony growth with cycloheximide | |
|---|---|
| Bacteria | Observation |
| *Lactobacillus brevis* - with cycloheximide | Growth - 1 distinct colony morphology |

TABLE 12-continued

Colony growth with cycloheximide

| Bacteria | Observation |
|---|---|
| *Lactobacillus brevis* - without cycloheximide | Growth - 1 distinct colony morphology |
| *Saccharomyces cerevisiae* - with cycloheximide | No growth |
| *Saccharomyces cerevisiae* - without cycloheximide | Growth - 1 distinct colony morphology |
| *Lactobacillus brevis* and *Saccharomyces* - with cycloheximide | Growth - 1 distinct colony morphology |
| *Lactobacillus brevis* and *Saccharomyces* - without cycloheximide | Growth - 2 distinct colony morphologies |

Example 12

Detection of Lactic Acid Bacteria from Beer Samples with Media Containing Cycloheximide Eight strains of LAB were obtained from commercial breweries and classified using a VITEK biochemical processor. The eight strains were classified as *Lactobacillus buchneri, Lactobacillus brevis* (2 strains), *Lactobacillus paracasei, Lactobacillus plantarum, Pediococcus acidilactici* and *Pediococcus damnosus* (2 strains). Additionally five strains of yeast were isolated and classified as Saccharomyces cerivisiae (4 strains) and Saccharomyces diastaticus.

Bacterial cultures of each strain of LAB were prepared as described in Example 7. The yeast cultures were prepared by inoculating pure cultures into Yeast Peptone Dextrose (BD; Franklin Lakes, N.J.) prepared according to the manufacturer's guidelines. The inoculated yeast cultures were incubated 18-24 hours aerobically at ambient temperature (about 24° C.).

Thin film culture plates (Plate IX) were hydrated with 1.0 ml Butterfields Buffer for 60 minutes before using.

The bacteria and yeast cultures were diluted to yield 10-250 cfu per plating media. Five different diluents were used as follows:

Diluent A—Butterfields Buffer (EdgeBiologicals; Memphis, Tenn.)
Diluent B—beer sample without yeast
Diluent C—beer sample without yeast
Diluent D—beer sample with brewing yeast
Diluent E—beer sample with brewing yeast Bacterial cultures (*L. buchneri, L. brevis* (2 strains), *L. plantarum, P. Acidilactici* and *L. Paracasei*) were diluted to obtain 10-250 CFU/media for Diluents D and E as follows:

1. Combine 0.01 mL of the culture with 99.0 ml Diluent A
2. Combine 0.02 ml Dilution 1 with 2.0 ml Diluent D (or E)
3. Combine 0.2 ml of Dilution 2 with 2.0 ml Diluent D (or E)
4. Combine 0.1485 ml Dilution 1 with 99.0 ml Diluent B (or C).

Dilutions for *P. damnosus* (2 strains) and the 5 yeast strains were prepared in the same manner except that 0.1 ml of the culture was diluted with 99.0 ml Diluent A.

For samples diluted in Diluent A2, D or E, 1.0 ml of Dilution 3 was inoculated directly onto Plate IX.

For samples diluted in Diluent A1, B or C, 30 ml of Dilution 4 were each filtered through a 0.45 μm mixed cellulose ester membrane (HAWG047S6 available from Millipore; Billerica, Mass.). The filters were placed onto Plate IX as described in Example 9.

The plates were incubated at 28 degrees Celsius in a 99.9% carbon dioxide incubator for 7 days. The plates were examined for the number of colony forming units and whether the plates were red or yellow indicating acid production. Results are shown in Table 13.

TABLE 13

Lactic Acid Bacteria Detection with cycloheximide in media

| | Method | | | | | |
|---|---|---|---|---|---|---|
| | Filtered | | | Direct | | |
| | Diluent | | | | | |
| | A1 | B | C | A2 | D | E |
| No Bacteria | 3*** | 0* | 0* | 0* | 0* | 0* |
| *L. plantarum* | ~150** | ~150** | ~100** | ~25** | ~40** | ~50** |
| *P. damnosus* (1) | ~50** | ~100** | ~100** | 0* | 0* | 0* |
| *L. paracasei* | ~100** | ~250** | ~250** | ~100** | ~100** | ~100** |
| *P. acidilactici* | ~100** | 100* | ~100** | ~100** | 0* | 0* |
| *S. cerevisiae* (1) | 0* | 0* | 0* | 0* | 0* | 0* |
| *S. cerevisiae* (2) | 0* | 1* | 0* | 0* | 0* | 0* |
| *S. cerevisiae* (3) | 0* | 0* | 0* | 0* | 0* | 0* |
| *S. diastaticus* | 0* | 0* | 0* | 0* | 0* | 0* |
| *S. cerevisiae* (4) | 0* | 0* | 0* | 0* | 0* | 0* |
| *P. damnosus* (2) | ~20** | 0** | 0** | ~100** | 0* | 0* |
| *L. buchneri* | ~100** | ~100** | ~100** | ~100** | ~100* | ~50* |
| *L. brevis* (1) | ~100** | ~100** | ~50** | ~25** | ~30* | ~20* |
| *L. brevis* (2) | ~100** | ~75** | ~100** | ~100** | ~100* | ~75* |

*Red
**Yellow
***Contaminated

Example 13

Detection of Lactic Acid Bacteria with Media Containing Nystatin

Overnight cultures of *Lactobacillus brevis, Pediococcus damnosus* and 5 strains of *Saccharomyces cerevisiae* were grown in MRS broth (bacteria cultures) or yeast peptone dextrose (YPD) broth (yeast cultures). These cultures were serially diluted, yielding suspensions that contained approximately 100 cfu/mL of the organisms. A second series of suspensions were prepared and 500 U/mL Nystatin (CAS No. 1400-61-9 from Sigma) were added to the suspensions. A stock solution was prepared by adding Nystatin solids to 100% ethanol to make a solution of 25,000 U/mL which was then added to the bacteria/yeast suspensions to obtain the desired Nystatin concentration. One milliliter of each of the different solutions was then inoculated onto Plate I. The inoculated plates were incubated at 28 degrees Celsius for 48-144 hr in a 99.9% CO2 incubator. The plates containing *Lactobacillus brevis* or *Pediococcus damnosus* colonies grew whether Nystatin was present or not. Plates containing *Saccharomyces cerevisiae* grew only on the plates that did not contain Nystatin.

Example 14

LAB Common in Foods on Thin Film Culture Plates

Overnight bacteria cultures of five bacteria strains were prepared as described in Example 7. The strains were obtained from commercial food processors and classified using a VITEK bioprocessor and identified as *Lactobacillus fermentum, Lactococcus lactis, Leuconostoc mesenteroides, Streptococcus mitis* and *Weissella viridescens*. The cultures were diluted to about 10 cfu (E1) or 100 cfu (E2) in Butterfields Buffer and inoculated onto Plate V and Plate VI.

Each of the cultures was also diluted in like manner except that the E1 nand E2 dilutions of the culture were mixed 1:1 with double-strength MRS broth containing 400 mg/L of Chlorophenol Red. These mixtures were then inoculated onto 3M PETRIFILM Aerobic Count plates.

The inoculated plates were incubated at temperatures of 25° C., 30° C., or 35° C. and checked for growth and the presence of acid at 24, 48 and, 72 hrs. The yellow zones indicating acid produced by the bacteria are given in either % of the plate that is yellow, or the number of distinguishable zones on the plate. The colonies are the number of cfu on the plate. Results are shown in Tables 14-18. The plate that is starred (*) is a 3M™ Petrifilm™ Aerobic Count Plate

TABLE 14

Detection of common LAB food contaminants - *L. mesenteroides*

| Dilution | Plate | Temp °C. | 24 Hours Yellow Zones | Colonies | 48 Hours Yellow Zones | Colonies | 72 Hours Yellow Zones | Colonies |
|---|---|---|---|---|---|---|---|---|
| 10 | * | 25 | 14 | 0 | 10 | 0 | 80% Yellow | 9 |
| 100 | * | 25 | 80% Yellow | 0 | 100% Yellow | 0 | 100% Yellow | 72 |
| 10 | Plate V | 25 | 14 | 7 | 50% Yellow | 23 | 80% Yellow | 23 |
| 100 | Plate V | 25 | 80% Yellow | 17 | 100% Yellow | 172 | 100% Yellow | 172 |
| 10 | Plate VI | 25 | 12 | 0 | 16 | 16 | 100% Yellow | 16 |
| 100 | Plate VI | 25 | 80% Yellow | 0 | 100% Yellow | 88 | 100% Yellow | 88 |
| 10 | * | 30 | 19 | 0 | 70% Yellow | 0 | 100% Yellow | 0 |
| 100 | * | 30 | 100% Yellow | 0 | 100% Yellow | 0 | 100% Yellow | 0 |
| 10 | Plate V | 30 | 17 | 17 | 17 | 17 | 100% Yellow | 17 |
| 100 | Plate V | 30 | 100% Yellow | 172 | 100% Yellow | 172 | 100% Yellow | 172 |
| 10 | Plate VI | 30 | 16 | 16 | 16 | 16 | 75% Yellow | 16 |
| 100 | Plate VI | 30 | 100% Yellow | 171 | 100% Yellow | 171 | 100% Yellow | 171 |
| 10 | * | 35 | 18 | 0 | 75% Yellow | 0 | 100% Yellow | 19 |
| 100 | * | 35 | 100% Yellow | 0 | 100% Yellow | 0 | 100% Yellow | 185 |
| 10 | Plate V | 35 | 24 | 24 | 24 | 24 | 100% Yellow | 24 |
| 100 | Plate V | 35 | 100% Yellow | 192 | 100% Yellow | 192 | 100% Yellow | 192 |
| 10 | Plate VI | 35 | 19 | 19 | 19 | 19 | 100% Yellow | 19 |
| 100 | Plate VI | 35 | 100% Yellow | 172 | 100% Yellow | 172 | 100% Yellow | 172 |

TABLE 15

Detection of common LAB food contaminants - *Lactococcus lactis*

| Dilution | Plate | Temp °C. | 24 Hours Yellow Zones | Colonies | 48 Hours Yellow Zones | Colonies | 72 Hours Yellow Zones | Colonies |
|---|---|---|---|---|---|---|---|---|
| 10 | * | 25 | 1 | 1 | 4 | 4 | 4 | 4 |
| 100 | * | 25 | 7 | 55 | 100% Yellow | 71 | 100% Yellow | 71 |
| 10 | Plate V | 25 | 0 | 3 | 5 | 5 | 5 | 5 |
| 100 | Plate V | 25 | 8 | 33 | 50% Yellow | 51 | 100% Yellow | 51 |
| 10 | Plate VI | 25 | 0 | 0 | 2 | 2 | 2 | 2 |
| 100 | Plate VI | 25 | 13 | 44 | 75% Yellow | 62 | 100% Yellow | 62 |
| 10 | * | 30 | 3 | 3 | 3 | 3 | 3 | 3 |
| 100 | * | 30 | 59 | 59 | 100% Yellow | 59 | 100% Yellow | 59 |
| 10 | Plate V | 30 | 5 | 6 | 6 | 6 | 6 | 6 |
| 100 | Plate V | 30 | 63 | 63 | 100% Yellow | 63 | 100% Yellow | 63 |
| 10 | Plate VI | 30 | 0 | 5 | 9 | 9 | 9 | 9 |
| 100 | Plate VI | 30 | 21 | 45 | 100% | 54 | 100% | 54 |
| 10 | * | 35 | 8 | 8 | 8 | 8 | 8 | 8 |
| 100 | * | 35 | 50% Yellow | 60 | 100% Yellow | 60 | 100% Yellow | 60 |

TABLE 15-continued

Detection of common LAB food contaminants - *Lactococcus lactis*

| Dilution | Plate | Temp °C. | 24 Hours Yellow Zones | Colonies | 48 Hours Yellow Zones | Colonies | 72 Hours Yellow Zones | Colonies |
|---|---|---|---|---|---|---|---|---|
| 10 | Plate V | 35 | 4 | 8 | 6 | 8 | 10 | 10 |
| 100 | Plate V | 35 | 50% Yellow | 66 | 100% Yellow | 66 | 100% Yellow | 66 |
| 10 | Plate VI | 35 | 3 | 6 | 6 | 6 | 7 | 7 |
| 100 | Plate VI | 35 | 20 | 46 | 75% Yellow | 46 | 100% Yellow | 46 |

TABLE 16

Detection of common LAB food contaminants - *Lactobacillus fermentum*

| Dilution | Plate | Temp °C. | 24 Hours Yellow Zones | Colonies | 48 Hours Yellow Zones | Colonies | 72 Hours Yellow Zones | Colonies |
|---|---|---|---|---|---|---|---|---|
| 10 | * | 25 | 0 | 0 | 0 | 0 | 4 | 6 |
| 100 | * | 25 | 0 | 0 | 0 | 0 | 75% yellow | 65 |
| 10 | Plate V | 25 | 0 | 0 | 0 | 0 | 0 | 0 |
| 100 | Plate V | 25 | 0 | 0 | 0 | 0 | 0 | 0 |
| 10 | Plate VI | 25 | 0 | 0 | 0 | 0 | 0 | 0 |
| 100 | Plate VI | 25 | 0 | 0 | 0 | 0 | 0 | 0 |
| 10 | * | 30 | 0 | 0 | 5 | 0 | 5 | 5 |
| 100 | * | 30 | 0 | 0 | 100% Yellow | 0 | 100% Yellow | 53 |
| 10 | Plate V | 30 | 0 | 0 | 0 | 0 | 1 | 4 |
| 100 | Plate V | 30 | 0 | 0 | 0 | 0 | 3 | 25 |
| 10 | Plate VI | 30 | 0 | 0 | 0 | 0 | 6 | 6 |
| 100 | Plate VI | 30 | 0 | 0 | 0 | 0 | 18 | 22 |
| 10 | * | 35 | 5 | 5 | 5 | 5 | 60% Yellow | 5 |
| 100 | * | 35 | 34 | 12 | 100% Yellow | 78 | 100% Yellow | 78 |
| 10 | Plate V | 35 | 0 | 0 | 3 | 4 | 4 | 4 |
| 100 | Plate V | 35 | 0 | 0 | 21 | 38 | 100% yellow | 38 |
| 10 | Plate VI | 35 | 0 | 0 | 4 | 5 | 6 | 7 |
| 100 | Plate VI | 35 | 0 | 0 | 1 | 16 | 75% Yellow | 22 |

TABLE 17

Detection of common LAB food contaminants - *Streptococcus mitis*

| Dilution | Plate | Temp °C. | 24 Hours Yellow Zones | Colonies | 48 Hours Yellow Zones | Colonies | 72 Hours Yellow Zones | Colonies |
|---|---|---|---|---|---|---|---|---|
| 10 | * | 25 | 0 | 0 | 0 | 0 | 1 | 0 |
| 100 | * | 25 | 0 | 0 | 0 | 0 | 13 | 0 |
| 10 | Plate V | 25 | 0 | 0 | 0 | 0 | 1 | 1 |
| 100 | Plate V | 25 | 0 | 0 | 0 | 0 | 3 | 4 |
| 10 | Plate VI | 25 | 0 | 0 | 5 | 1 | 5 | 5 |
| 100 | Plate VI | 25 | 0 | 0 | 9 | 1 | 10 | 6 |
| 10 | * | 30 | 0 | 0 | 2 | 0 | 3 | 0 |
| 100 | * | 30 | 0 | 0 | 11 | 0 | 16 | 7 |
| 10 | Plate V | 30 | 0 | 0 | 0 | 0 | 0 | 0 |
| 100 | Plate V | 30 | 0 | 0 | 0 | 0 | 0 | 6 |
| 10 | Plate VI | 30 | 0 | 0 | 0 | 0 | 0 | 0 |
| 100 | Plate VI | 30 | 0 | 0 | 0 | 0 | 9 | 9 |
| 10 | * | 35 | 0 | 0 | 0 | 0 | 2 | 0 |
| 100 | * | 35 | 0 | 0 | 0 | 0 | 7 | 0 |
| 10 | Plate V | 35 | 0 | 0 | 0 | 0 | 0 | 0 |
| 100 | Plate V | 35 | 0 | 0 | 4 | 7 | 4 | 9 |
| 10 | Plate VI | 35 | 0 | 0 | 0 | 0 | 0 | 0 |
| 100 | Plate VI | 35 | 0 | 0 | 0 | 0 | 0 | 0 |

TABLE 18

Detection of common LAB food contaminants - *Weissella viridescens*

| Dilution | Plate | Temp °C. | 24 Hours Yellow Zones | Colonies | 48 Hours Yellow Zones | Colonies | 72 Hours Yellow Zones | Colonies |
|---|---|---|---|---|---|---|---|---|
| 10 | * | 25 | 0 | 0 | 24 | 0 | 60% Yellow | 26 |
| 100 | * | 25 | 0 | 0 | 90% Yellow | 0 | 100% Yellow | 213 |
| 10 | Plate V | 25 | 0 | 0 | 0 | 0 | 0 | 0 |
| 100 | Plate V | 25 | 0 | 0 | 0 | 0 | 0 | 0 |
| 10 | Plate VI | 25 | 0 | 0 | 0 | 0 | 0 | 0 |
| 100 | Plate VI | 25 | 0 | 0 | 0 | 0 | 0 | 0 |
| 10 | * | 30 | 0 | 0 | 26 | 0 | 100% Yellow | 26 |
| 100 | * | 30 | 0 | 0 | 100% Yellow | 0 | 100% Yellow | 222 |
| 10 | Plate V | 30 | 0 | 0 | 0 | 0 | 0 | 0 |
| 100 | Plate V | 30 | 0 | 0 | 0 | 0 | 0 | 0 |
| 10 | Plate VI | 30 | 0 | 0 | 0 | 0 | 0 | 0 |
| 100 | Plate VI | 30 | 0 | 0 | 0 | 0 | 0 | 0 |
| 10 | * | 35 | 0 | 0 | 60% Yellow | 0 | 100% Yellow | 32 |
| 100 | * | 35 | 0 | 0 | 100% Yellow | 195 | 100% Yellow | 195 |
| 10 | Plate V | 35 | 0 | 0 | 0 | 0 | 0 | 0 |
| 100 | Plate V | 35 | 0 | 0 | 0 | 0 | 0 | 0 |
| 10 | Plate VI | 35 | 0 | 0 | 0 | 0 | 0 | 0 |
| 100 | Plate VI | 35 | 0 | 0 | 0 | 0 | 0 | 0 |

Example 15

Detection of LAB in Food

Bacteria cultures were prepared and diluted as described in Example 14 except that the dilutions were made with 0.1% peptone water. A mixture containing all five of the organisms (with a total of 1000-10,000 cfu) was inoculated into commercially available French dressing having a pH of about 4.

Approximately 11 grams of inoculated salad dressing was mixed with 99 ml of 0.1% peptone water in a stomacher at 230 RPM for 1 minute. A 1:10 dilution was taken from this bag. Further dilutions were performed to obtain 1:100 and 1:1000 dilutions with 0.1% peptone water. The pH of each of the samples was adjusted to 6.5+/−0.2 using 1 M HCl, and then inoculated onto the Plate V (denoted Plave V in Table 19.

Each of the cultures was also diluted in like manner except that the last dilution was made in 50-50 mixture of MRS broth containing 200 mg/L of Chlorophenol Red and the diluted culture. The diluted cultures were inoculated onto 3M PETRIFILM Aerobic Count plates (AC) as described in Example 1. These plates are denoted AC in Table 19.

A second series of plates was tested without adjusting the pH of the sample which was about 4. All of the inoculated plates were incubated at 30° C. for 24, 48, and 72 hours. Colonies were detected as red dots in the plate surrounded by an acid zone. The plates were inspected for colony counts for each plate and results are shown in Table 19.

TABLE 19

Bacteria counts in French Dressing

| Initial Bacteria Inoculation | Dilution | Counts - 24 hrs Plate V | AC | Counts - 48 hrs Plate V | AC | Counts - 72 hrs Plate V | AC |
|---|---|---|---|---|---|---|---|
| pH ~ 4.0 ± 0.2 | | | | | | | |
| 0 | 1:10 | 0 | 0 | 0 | 0 | 0 | 0 |
| 0 | 1:100 | 0 | 0 | 0 | 0 | 3 | 0 |
| 0 | 1:1000 | 0 | 0 | 0 | 0 | 1 | 0 |
| ~10cfu-100cfu | 1:10 | 0 | 0 | 30 | 38 | 32 | 46 |
| ~10cfu-100cfu | 1:100 | 4 | 0 | 4 | 1 | 7 | 1 |
| ~10cfu-100cfu | 1:1000 | 0 | 0 | 0 | 0 | 1 | 0 |
| ~100cfu-1000cfu | 1:10 | 2 | 0 | 103 | 37 | 103 | 37 |
| ~100cfu-1000cfu | 1:100 | 18 | 3 | 21 | 6 | 24 | 24 |
| ~100cfu-1000cfu | 1:1000 | 0 | 0 | 2 | 0 | 5 | 1 |
| pH ~ 6.5 ± 0.2 | | | | | | | |
| 0 | 1:10 | 0 | 0 | 0 | 3 | 2 | 4 |
| 0 | 1:100 | 0 | 0 | 0 | 0 | 4 | 0 |
| 0 | 1:1000 | 0 | 0 | 0 | 0 | 2 | 0 |
| ~10cfu-100cfu | 1:10 | 24 | 15 | 55 | 39 | 55 | 39 |
| ~10cfu-100cfu | 1:100 | 3 | 0 | 10 | 0 | 12 | 1 |
| ~10cfu-100cfu | 1:1000 | 0 | 0 | 0 | 0 | 3 | 0 |
| ~100cfu-1000cfu | 1:10 | 139 | 83 | 139 | 83 | 139 | 83 |
| ~100cfu-1000cfu | 1:100 | 18 | 6 | 32 | 6 | 32 | 28 |
| ~100cfu-1000cfu | 1:1000 | 3 | 0 | 7 | 0 | 10 | 1 |

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

What is claimed is:

1. A method comprising:
   providing a thin film culture device comprising a culture medium to support growth of acid-producing bacteria and a cold water-soluble gelling agent, a carbohydrate that can be fermented by the acid-producing bacteria, a sample, and a pH indicator with a transition range that extends below pH 7.0;
   combining, in the culture device, a predetermined volume of the sample, the culture medium, the pH indicator, and the fermentable carbohydrate;
   incubating the culture device for a period of time; and detecting the presence or absence of a microorganism;
wherein detecting the presence or absence of a microorganism comprises detecting the presence or absence of an acid-producing microorganism.

2. The method of claim 1, wherein the pH of the culture medium in the provided thin film culture device is less than 6.5.

3. The method of claim 1, wherein the provided thin film culture device further comprises a selective agent.

4. The method of claim 3, wherein the selective agent is an antifungal agent.

5. The method of claim 4 wherein the antifungal agent is selected from the group consisting of Cycloheximide, Nystatin, Natamycin, Amphotericin B, Filipin, and combinations thereof.

6. The method of claim 1, further comprising differentiating the acid-producing bacteria, wherein said differentiating comprises detecting production of carbon dioxide gas by individual colonies.

7. The method of claim 1, wherein said incubating is carried out aerobically.

8. The method of claim 1, wherein said incubating is carried out anaerobically.

9. The method of claim 1, further comprising combining the sample with a diluent capable of neutralizing a chemical sanitizer.

10. The method of claim 1, further comprising:
providing an imaging system; and
obtaining an image of a growth area of the culture device;
wherein said detecting comprises displaying, printing, or analyzing the image of the growth area.

11. The method of claim 10, wherein the imaging system comprises an illumination source and wherein said obtaining comprises illuminating the growth area.

12. The method of claim 1, further comprising the step of enumerating microorganisms.

13. The method of claim 12, wherein said enumerating microorganisms comprises enumerating two or more types of microorganisms.

14. The method of claim 1 wherein the pH indicator is bromcresol purple, bromphenol blue, chlorophenol red, or bromcresol green.

15. The method of claim 1 wherein the acid-producing bacteria is *Acetobacter* or a lactic acid-producing bacteria.

* * * * *